(12) United States Patent
Abba et al.

(10) Patent No.: US 8,129,464 B2
(45) Date of Patent: Mar. 6, 2012

(54) LOW APPLICATION TEMPERATURE HOT MELT ADHESIVE

(75) Inventors: Fabienne Abba, Compiegne (FR); Christopher Morel-Fourrier, Paris (FR); Nicolas Edgard Sajot, Wauwatosa, WI (US)

(73) Assignee: Bostik, Inc., Wauwatosa, WI (US)

( * ) Notice: Subject to any disclaimer, the term of this patent is extended or adjusted under 35 U.S.C. 154(b) by 0 days.

(21) Appl. No.: 12/476,940

(22) Filed: Jun. 2, 2009

(65) Prior Publication Data

US 2009/0264580 A1    Oct. 22, 2009

Related U.S. Application Data

(63) Continuation of application No. 11/251,256, filed on Oct. 14, 2005, now abandoned.

(51) Int. Cl.
*C08L 53/02* (2006.01)

(52) U.S. Cl. ........ 524/505; 524/474; 524/487; 524/488; 524/499

(58) Field of Classification Search .................. 524/474, 524/487, 488, 499, 505
See application file for complete search history.

(56) References Cited

U.S. PATENT DOCUMENTS

| | | | |
|---|---|---|---|
| 4,914,253 A | 4/1990 | Chang | |
| 5,143,968 A | 9/1992 | Diehl et al. | |
| 5,149,741 A | 9/1992 | Alper et al. | |
| 5,266,394 A | 11/1993 | Diehl et al. | |
| 5,275,589 A | 1/1994 | Bozich | |
| 5,939,483 A | 8/1999 | Kueppers | |
| 6,180,229 B1 | 1/2001 | Becker et al. | |
| 6,184,285 B1 | 2/2001 | Hatfield et al. | |
| 6,319,979 B1 | 11/2001 | Dubois et al. | |
| 6,465,557 B1 | 10/2002 | De Keyzer et al. | |
| 6,818,093 B1 | 11/2004 | Taal et al. | |
| 2003/0139516 A1 | 7/2003 | Quinn et al. | |
| 2005/0176867 A1 | 8/2005 | He et al. | |
| 2005/0181207 A1 | 8/2005 | He et al. | |
| 2005/0182183 A1 | 8/2005 | He et al. | |
| 2005/0182194 A1 | 8/2005 | He et al. | |
| 2006/0229411 A1 | 10/2006 | Hatfield et al. | |

FOREIGN PATENT DOCUMENTS

| | | |
|---|---|---|
| EP | 0532831 | 3/1993 |
| EP | 0451919 | 2/1995 |
| EP | 0734426 | 9/1998 |
| EP | 0451920 | 7/1999 |
| EP | 0798358 | 7/2002 |
| EP | 0900258 | 6/2003 |
| WO | 97/10310 | 3/1997 |
| WO | 97/19582 | 6/1997 |
| WO | 97/33921 | 9/1997 |
| WO | 98/02498 | 1/1998 |
| WO | 98/03603 | 1/1998 |
| WO | 99/13016 | 3/1999 |
| WO | 00/78886 | 12/2000 |
| WO | 2004/035705 | 4/2004 |
| WO | 2005/063914 | 7/2005 |

OTHER PUBLICATIONS

PCT International Search Report, European Patent Office, Mar. 12, 2007, PCT/US2006/039471.

*Primary Examiner* — Peter Szekely
(74) *Attorney, Agent, or Firm* — Andrus, Sceales, Starke & Sawall, LLP

(57) ABSTRACT

A hot melt adhesive composition, comprising a blend of components including about 10% to about 40% by weight of an elastomeric block copolymer, preferably styrene-isoprene-styrene (SIS) or styrene-butadiene-styrene (SBS), about 15% to about 70% by weight of a first midblock tackifying resin having a softening point of at least about 110° C. and having an aromatic content of at least about 1.5% by weight; about 0 to 55% of second midblock tackifying resin, about 5% to about 35% by weight of a plasticizer; and about 0% to about 20% by weight of an end block resin having a softening point lower than 125° C.; wherein the components total 100% by weight of the composition, the viscosity of the composition is equal to or less than about 20,000 mPa·s at 120° C., and is applied at a temperature lower that 150° C. and initial bond retention of the composition on elastic strands is at least about 60%. Also, the elastic modulus G' of the composition is higher than about 5000 Pa, the vicous modules G" is higher than about 50 Pa, and the tan delta value is between about 0.5 and about 60. Laminates, especially those used in disposable soft goods, and methods of making such laminates are also described. The adhesive composition and/or laminate may be used in making a variety of end products such as a disposable diaper, a sanitary napkin, a bed pad, a bandage, a surgical drape, a tape, a label, a plastic sheet, a nonwoven sheet, a paper sheet, a cardboard, a book, a filter, or a package.

92 Claims, 2 Drawing Sheets

LOW APPLICATION TEMPERATURE HOT MELT ADHESIVE

CROSS-REFERENCE TO RELATED APPLICATIONS

This application is a continuation of U.S. application Ser. No. 11/251,256 filed on Oct. 14, 2005, now abandoned.

BACKGROUND OF THE INVENTION

The present invention relates to hot melt adhesives, and more particularly to a hot melt adhesive having low viscosity and showing good cohesion level like high initial bond resistance that may be applied at relatively low temperatures for example for making elastic components such as laminates containing elastic strands for use in disposable diapers.

The increasing complexity of manufactured goods, in particular disposable goods, also leads to major improvements and developments in the hot melt adhesive industry. Hot melt adhesives are being used to bond a wider variety of substrates, within a broader adhesive application process window, and for a large end-use portfolio. For example considering the diaper manufacturing industry, materials involved may be non-woven materials, polymeric films, and in general elastomeric components. These elastomeric components can be used in products like diapers, in a form of strands, films, nonwovens or any other continuous or discrete form.

Processability of hot melt adhesive is linked to their ability to be melted, and transported and/or coated in a molten stage to the final location where the bond is required. Usually the molten adhesive is sprayed, or coated as a film. Once cooled down, the adhesive needs to fulfill multiple requirements, like bond strength measured by peel force or bond retention under or after mechanical stress, and under or after various thermal conditions.

Typically hot melt adhesives can be based on polymers such as polyolefins (ethylene- or propene-based polymers), or functionalized polyolefins (ethylene or propene copolymers with oxygenated function containing monomers), or styrene block copolymers containing at least one rubbery phase, like SIS, or SBS. Styrene block copolymers are of interest due to their dual characteristics, i.e. cohesion of the styrenic phase associated with the rubber behavior of another phase. Typical application temperatures are equal to or higher than 150° C.

Combining parameters in the areas of a substrate's nature, adhesive processability and a product's end use requirements, there has been a steady trend in the industry to change and use more sophisticated substrate types, for technical or economical reasons. This can lead to the use of more sensitive substrate materials, in terms of mechanical, thermal, weather or time resistance, with the need to not compromise any of the other attributes, i.e. the overall manufacturing process should remain of the same concept, and the end use of the item should be fulfilled in the same way, or enhanced. For example in the diaper industry, typical application temperatures for elastic attachment would be around 163° C. Depending on the bonding performances required, however, it may be higher. Lowering the application temperature presents problems in terms of wet-out, and most of the time 150° C. would be seen as a minimum temperature one can go to attach elastic parts onto the diaper structure.

It is known in the diaper industry that the use of heat sensitive substrates may cause problems if the adhesive temperature is too high because the production line has to be stopped each time the substrate breaks or is damaged by the molten adhesive material (described as a "burn through" phenomenon) and would need to be replaced or fixed before starting the line again. This may also be the case with non-woven substrates or with elastomeric components used in the diaper structure. Thus, a lower application temperature of the hot melt adhesive would be very helpful to avoid maintenance issues and downtime on production lines.

Another factor making it desirable to reduce the application temperatures of hot melt adhesives is that the diaper industry has been trying to use thinner gauge films in order to decrease the overall diaper's material weight, and consequently the material cost. Over the years, this has been achieved with more or less success, depending on the difficulty to keep both the manufacturing process and end-use attributes the same. Heat distortion or deterioration of the film or non-woven substrates can occur easily when the hot adhesive material contacts the substrates' surfaces. As a result, the functionality of the substrates in the end-use structure is affected in a way that is not acceptable. Among other reasons to decrease the application temperature of the hot melt adhesives is the concern of saving some energy cost needed to heat the adhesive material, as well as the need to enhance safety for the workers on the production line to minimize potential burn hazards.

Many references offer possible solutions to apply a hot melt adhesive material at low temperature. Lowering material viscosity is very often seen as the only criterion to lower the application temperature. Both lack of cohesion and incompatibility of composition ingredients, however, have hindered solving this problem in the manner in which the present invention proposes to solve the problem.

It has to be noted that the phrase "low application temperature hot melt adhesive" as used herein corresponds to the ability to apply the molten or deformable adhesive material at a relatively low process temperature, or "application temperature", i.e. less than 150° C., in order to build a bond between two substrates. Sometimes prior art references utilize the phrase "low temperature" as a term to qualify adhesive materials presenting good mechanical and adhesive performances at low temperatures into the finished good once the bonding process has been made. These low temperatures are usually lower than room temperature, but it is not the intent of the present invention to deal with this specific requirement.

Adhesive application at low temperature is relatively easily achieved for specific applications or application domains where there is no harsh cohesion required. Although focus could be put on Shear Adhesion Failure Temperature (SAFT) value, the aim of this test is more in defining a failure under a constantly increasing temperature than reflecting the mechanical resistance of the bond over time. Many references exhibit interesting SAFT values that do not correlate with the ability of the adhesive materials to resist creep conditions over an extended period of more than few minutes at elevated temperature.

For example, U.S. Pat. No. 6,180,229 B1 is focused on the very narrow process engineering domain of a screen roller or an engraved roller to provide discontinuous coatings of any Hot Melt Pressure Sensitive Adhesive (HMPSA). The application areas are feminine napkin, bandages, tapes, where intended internal cohesion of the adhesive does not need to be high, as the described formulae examples contain more than 30% of an oil. Using this amount of oil at the viscosity level claimed, i.e. less than 5,000 mPa·s at 125° C., it is clear that this reference does not teach how to achieve a conventional elastic attachment at low temperature. No mention is made about spraying the adhesive material at low temperature on elastic strands and in-between thin film substrates in order to hold these elastic strands in place over time.

EP 0 451 919 B1 and EP 0 451 920 also do not mention any potential for the adhesive materials to hold elastic strands in a diaper structure. Although they mention that maintaining adhesion in elastically demanding applications is generally the role of styrenic block copolymer based adhesives, there is no discussion in either of these references about how to achieve a conventional elastic attachment at low application temperature.

U.S. Pat. No. 5,275,589 describes how to bond a polyolefinic film to a non-woven substrate to achieve the construction of what is known in the diaper industry as a cloth-like back sheet. This reference describes a coating process with an adhesive containing substantially no oil. Even if the application temperature was low, the viscosity level of the examples described in this patent would be very high and would thus hinder any process where the adhesive needed to be pumped and pushed through conventional components of a hot melt adhesive application device.

U.S. Pat. No. 6,465,557 B1 claims an adhesive that can be used at low temperature. The potential uses for the adhesive set forth in the description is clearly remote from any higher cohesion demanding application, i.e. the adhesive is stated to be useful for being applied to a release liner and transfer coated to a garment, for use in a feminine pad, panty shield, or diaper inserts. As such, these adhesives are pressure sensitive adhesives (PSA).

EP 0 798 358 B1 is focused on bottle labeling applications, where elevated temperature storage conditions and long open times are required. Again, this does not help to get bond retention in the way needed for elastic attachment in a diaper structure.

U.S. Pat. No. 6,818,093 B1 is very specific to construction applications in which dermatologically-compatible coatings are present on substrates. This reference proposes an interesting way to enhance the adhesion level of adhesives, as it is well know that the dermatological compatible coating affects the surface nature of the substrates and the ageing effect of adhesive bonding. Although this reference mentions that hot melt adhesives for structural or elastic attachment are available on the market, it does not provide any solution to applying them at low temperatures for elastic attachment.

WO 97/10310 mentions adhesive systems that can be applied at temperatures as low as 121° C., and having a very high diblock content in the polymer component. This is typical of non-cohesive systems in that the diblock structure provides a tendency for the adhesive material to creep upon ageing, due to temperature or mechanical stress.

WO 00/78886A1 mentions applications at low temperatures of 130° C. to 135° C. Unfortunately, application results are exhibited only for spiral construction or bottle labeling, which are non-demanding applications in terms of cohesion and bond retention, in contrast to the ones needed in an elastic attachment environment. A cohesive adhesive formula is shown in an example, but its viscosity level at 135° C. does not lead one to think this material can be easily applied at this temperature or below.

Whenever the focus is to obtain cohesion for bond retention or creep resistance, for example for elastic attachment in a diaper structure, the sophistication level into the adhesive formulation needed to achieve this goal is high, and systematically not reached in the way this present invention presents it. For example, U.S. Pat. No. 6,180,229 B1 proposes to coat adhesives at temperatures ranging from 90° C. to 140° C. It describes formula examples containing more than 30% of oil. Besides the fact that such amounts are not practical to maintain bond retention in a hot melt adhesive composition, it describes aromatic modified resins having a softening point approximately equal to or lower than 100° C., which leads to poor cohesion levels, non-aromatic modified resins having a softening point in a broad range of temperature (100 to 140° C.), which lead to bad adhesion levels, and use of pure aromatic resins with softening points greater than about 100° C., which is directionally opposite to the present invention.

EP 0 451 919 B1 and EP 0 451 920 propose polymer structures to coat adhesive at temperature as low as 121° C. These references exhibit formulas with specific polymers that are present at a level of 25% or more in the formulation, with an oil content from 0 to 25%, preferably from 0 to 15%. These conditions are remote from low viscosity products with the conditions the present invention proposes. No mention is made of the resin nature or softening point, except a general statement and examples that a 95° C. softening point resin is usable, and only mentioning that resins with softening points of 80 to 115° C. could be used.

WO 2004/035705 A2 covers the use of waxes, specifically microcrystalline waxes from 1 to 10%, to allow the viscosity of the composition to be lower than 10,000 mPa·s at 120° C., and to allow adhesive coating at below 120° C. No specific description of formulas is reported, but comparisons are made between compositions corresponding to different amounts and natures of wax. The reference discusses various test methods, i.e. a specific cube flow test, aged peel test, and G' measurement which do not teach how to properly achieve bond retention in a given application.

WO 99/13016 presents a way to enhance specific adhesion, using a fatty acid oil and/or a natural oil in a hot melt adhesive composition. This allows for a lower application temperature as low as 100° C. to 130° C. This solution may not provide any economic advantage over current technology using conventional synthetic mineral oils, and does not teach how to make a hot melt composition that would be adapted to creep resistance or bond retention in general, and elastic attachment into a diaper structure in particular.

U.S. Pat. No. 5,275,589 proposes to apply hot melt adhesive at around 107° C. with the specific feature of obtaining a non tacky coating. The adhesive contains substantially no oil. Moreover, it is shown in the examples that low softening point resins are used to soften or make the polymer grades thinner. The targeted resin's softening point window, obtained by mixing several resins together, is from 25 to 50° C., which again is not compatible with an adhesive material getting acceptable creep resistance performances in general.

U.S. Pat. No. 6,465,557 B1 exhibits formulas where oil content is very high, higher than 25% and sometimes higher than 30%. Resins exhibited in the examples have a softening point of around 100° C., which prevents an acceptable bond retention of the adhesive bond at elevated temperature in the sense the present invention is showing it.

U.S. Pat. No. 6,184,285 B1 describes an adhesive composition having acceptable bond performances both at low and high testing temperatures. This uses a specific combination of polymer grades, and exhibits no high softening point resin, although it mentions that any conventional resin can be used. This reference does not focus specifically on solving creep resistance or bond retention issues.

US 2005/0176867 A1 claims formulas that are applied at 135° C., with no relevant mention or preference according to the softening point level of the cited tackifying resins, both midblock resins and end-block resins, which is a major characteristic of these ingredients to give cohesion to the final adhesive bond. Preferred midblock tackifying resins are said to have a softening point higher that 25° C., which is the majority of existing tackifying resins. Among a long description of conventional resins, mention is made of aliphatic petroleum hydrocarbon resins with softening points of from 70 to 135° C., which again is a very general description. Mention is also made of alicyclic petroleum hydrocarbon resins, aliphatic/aromatic or cycloaliphatic/aromatic resins and hydrogenated derivatives, with no mention of the softening points. Also, mention is made of preferred mid-block tackifying resins like Wingtack 95, Hercures C, Eastotac H100R, Escorez 5600, all having a softening point around 100° C. No mention is made about the aromatic/aliphatic nature of these resins, except that aliphatic ones are preferred. Concerning end-block tackifying resins, no mention is made about the softening point range that would be adequate to use.

WO 97/10310 focuses on the use of diblock structures to provide the right level of adhesion, without considering a specific and relevant domain for the tackifying resins' chemistry. Low to medium softening point mid-block resins are described, and no substantially aromatic resins are mentioned and none are exhibited.

WO 00/78886A1 claims adhesive formulas which all contain some additive like surfactants or polyether derivatives. Based on this peculiar feature, this reference does not bring any relevance to the present invention.

WO 98/02498 claims the use of wax materials to achieve low application temperatures in packaging applications. Moreover, resins mentioned in the examples have softening points of 100° C. or below, which does help with decreasing the viscosity of the adhesive, but not building enough cohesion in it. There is also some examples with a non aromatic 130° C.—softening point resin which do not show anything different from the examples where softening points are maintained at 100° C. or lower.

WO 2005/063914 A2 focuses on low viscosity hot melt adhesive using SIBS polymer and also including among other constituents mid-block tackifying resins, potentially having an aromatic character, and with softening point not higher than 95° C.

U.S. Pat. No. 6,818,093 B1 is very specific to construction applications in which some dermatologically-compatible coatings are present on substrates. This reference exhibit examples of formulas containing either low molecular weight polymer like a diblock structure SI, or low softening point mid-block resins. This interesting way to decrease cohesion and viscosity of the formulation does not correspond to what the present invention intends to do.

EP 0 798 358 B1 is focused on bottle labeling applications and claims low viscosity levels, and shows examples with high amounts of an oil plasticizer. Resins shown in the examples have softening points of approximately 100° C.

U.S. Pat. Nos. 5,266,394 and 5,143,968 mention the use of any tackifying resin having a softening point above 70 and below 150° C. They describe viscosity levels in the examples at 130° C., where the tackifying resin has a melting point of approximately 100° C.

EP 0900258 B1 is another reference describing some specific polymer features in a hot melt composition where only a 100° C. softening point resin is used. Interesting viscosity levels are reached at 130° C. but the compositions are outside of the domain the present invention.

Numerous references claim the concept of applying an adhesive at low temperature, with a certain lack of precision, i.e. they do not precisely define the temperature domain, or they do not give a clear way of how to practically achieve the low temperature application.

For example WO 98/02498 claims to achieve low application temperatures in the packaging area, which temperatures are intended to be lower than 150° C., but then also referred to be 135° C. and above. This is not sufficient to teach how to build cohesion in the adhesive material while having a low application temperature.

US 2005/0176867 A1 claims formulas that are applied at 135° C. with the use of conventional hot melt adhesive raw materials, and also with the use of additives as ionomer resins, for example for elastic attachment applications. 135° C. is not a low temperature for applying a hot melt adhesive, even for an adhesive based on thermoplastic elastomers like SIS, SBS and other polymers, as this temperature is currently used in many applications, including diaper manufacturing. In this reference, it is also mentioned that applications at a temperature as low as 93° C. can be achieved, but no description is given, even in the examples. In the examples, formulas are applied at 135° C., showing interesting creep resistance performances in elastic attachment, although no good indication is provided about adhesive add-on levels, as the width of the adhesive patterns is not specified. In the same examples, only where ionomer resins are used, it is stated that these formulas can be applied at temperatures lower than 135° C., but it is not shown, and it is further not shown that it could be done for elastic attachment. This reference is of no help in what the present invention intends to show, as it is mainly focused on the use of ionomer resin, and as it does not teach how to use hot melt raw materials in conjunction with elastic attachment made effectively at application temperatures lower than 135° C., and with effectively good creep resistance performances.

U.S. Pat. No. 6,465,557 B1 claims to run low temperature applications with no real precision on the temperature level achievable. The description of adhesive composition given in this reference does not allow one to think about a relevant way to get creep resistance from the bond with acceptable performances.

U.S. Pat. No. 6,184,285 B1 claims specific adhesive formulations that can be applied at about 135° C. or higher temperatures. Although it exhibits viscosity measurements at temperatures as low as 100° C., it does not show that this low level of temperature is achieved while applying the adhesive.

EP 0734426B1 focuses on low viscosity hot melt formulations but claims an application temperature of 150 to 200° C. This is outside of the domain the present invention.

WO 2005/063914 A2 claims low viscosity hot melt adhesives, with viscosities at or lower than 80,000 mPa·s at 177° C. Moreover, casting a film of adhesives materials in solvents is the method used for all the coating applications shown by this reference. No illustration of a potentially low process temperature for applying the adhesive is depicted, or discussed.

Aromatic resins, including pure monomer resins, are commonly used raw materials to formulate hot melt adhesives, those being PSA or not. The softening point of these materials is typically between 5° C. and 160° C., and their presence in the formulas can be driven by the level of tack and of adhesion required, as well as by the need to reinforce the styrenic phase of any styrenic block copolymer. Reinforcing resins help to provide a higher cohesion to the adhesive bond, at room temperature as well as at elevated temperature.

For example WO 97/19582 mentions the use of aromatic resins or pure monomer resins to reinforce the Tg of the styrene phase. This is very typical of the intent to use this kind of resin to enhance the level of cohesion of the adhesive material, with no emphasis on the level of viscosity that the presence of the resin is generating. Furthermore, there is typically no link with the need of applying the adhesives at low temperature. In this reference, no teaching is exhibited to help understand how or why low viscosity products made this way could be applied at low temperature.

WO 00/78886A1 mentions the use of Hercolite 290, which is a high softening point aromatic resin that helps to build cohesion into the adhesive material, as pure monomer resins are known for, but definitively does not help with lowering the application temperature.

The same remark can be said of US 2005/0181207, WO 2005/0182183 A1, and WO 2005/0182194 A1. Each of these references claim compositions for elastic attachment, which can use pure monomer resins of low/medium to high softening points, and specify a process temperature of 143° C. to 163° C. to apply hot melt adhesives according to the invention. This is evidence that no link has been made between low application temperature and low to medium softening point aromatic resins.

In US 2005/0176867 A1, aromatic resins, including pure monomer resins, are mentioned as a potential component of the adhesive formulas. First, these resins, as conventional ingredients widely used in typical hot melt formulation, are described in this reference in the same way other conventional ingredients are described like polymers, mid-block tackifying resins, and waxes, and no link is made to the fact that their presence is necessary or useful for their use in low application temperature formulations. Then, when it comes to a preferred hot melt composition in the detailed description of the invention, the use of a end-block compatible resin is mentioned, but only expressly in conjunction with the presence of an ionomer resin, from 0.1 to 40%. Finally, no mention or preference is made for the softening point value of the cited tackifying resins, both mid-block resins and end-block resins. Softening point of such tackifying resins is an essential characteristic of these ingredients in regard to low application temperature and is a key parameter for the present invention. These three last points show that the information disclosed in this reference is unable to teach one skilled in this art anything that would bring any relevance to the present invention.

None of the cited references claims any specific resin features based on composition, aromatic/aliphatic balance and softening point level to reach the right adhesion performances as described and claimed in the present invention. There is no relevance to be found in them according to the solution that the present invention has developed.

SUMMARY OF THE INVENTION

The present invention solves the very important requirement of having a hot melt adhesive applied at relatively low application temperature, i.e. under 150° C., using the same application techniques as currently used, like coating techniques and add-on levels, and providing the end-use application the same level of performances expected with the current technologies, i.e. high bond strength levels in term of creep resistance, peel force and in general bond retention with mechanical resistance and heat resistance. The present invention is based on a unique formulation using styrene block copolymers, particularly for elastic attachment into diaper structures.

Various methods are conventionally used to coat a hot melt adhesive at fairly low viscosity on a substrate. This can be made by roll coating or any printing type method, or by slot coating, by extrusion or by spray gun. Spray gun techniques are numerous and can be done with or without assistance of compressed air that would shape the adhesive spray, and consequently the adhesive pattern. The hot melt adhesive material is generally allowed to melt in tanks, and then pumped through hoses to the final coating spot on the substrates. For the present invention, preferred methods of applying the adhesive would be by spray application, most preferably assisted by air. Among these techniques, the most common are spiral spray (Controlled Fiberization™ by Nordson), Summit™ by Nordson, Surewrap™ by Nordson, Omega™ by ITW, Curtain Coating™ by Nordson and melt blown process.

For the present invention, the temperature at which the hot melt adhesive is applied should be below 150° C., so that the heat sensitive substrates would not be damaged. Preferably, this temperature should be equal to or lower than 140° C., most preferably lower than 135° C.

Also, the viscosity of the adhesive material needs to be generally lower than 20,000 mPa·s, more preferably lower than 15,000 mPa·s, most preferably lower than 12,000 mPa·s measured at 120° C. An adhesive with such low viscosity is needed to be operated through standard hot melt adhesive equipment and to achieve the right pattern and consequently the right bonding performances at the application temperature.

The adhesive of the present invention can be used with any process of conventional or non-conventional elastic attachment technology as known in the state of the art.

The adhesive of the present invention can be used with any application where various substrate materials are involved like non-woven materials, polymeric films, and in general elastomeric components put in items like diapers, in the form of strands, films, nonwovens or any other continuous or discrete form. Any substrate material and any substrate form could be used in any combination possible, the adhesive allowing to bond two or more substrates together. The substrates can be of multiple forms for example fiber, film, thread, strip, ribbon, coating, foil, sheet, and band. The substrate can be of any known composition for example polyolefin, polyacrylic, polyester, polyvinyl chloride, polystyrene, cellulosic like wood, cardboard and paper, or made out of mineral compounds like concrete, glass or ceramics. The substrate's mechanical behavior can be rigid, plastic or elastomeric. Among elastomeric material are various examples like natural or synthetic rubber, polyurethane based copolymers, polyether or polyester urethanes, block copolymers of styrene or of amides, or olefinic copolymers. The above lists are not limitative or all-inclusive, but are only provided as common examples. In the present invention, various methods to process hot melt adhesives can be employed, linked to their ability to be melted, and transported and/or coated or sprayed in a molten stage to the final location where the bond is required.

The adhesive of the present invention can also be used with any application where composites and disposable products are made with the help of bonding parts together with a hot melt adhesive used at a temperature lower than 150° C., preferably equal to or lower than 140° C., most preferably lower than 135° C., while obtaining adequate cohesion from the adhesive bond to withstand mechanical stress at low, ambient or elevated temperature, in particular under creep conditions. Diaper, adult incontinence products, sanitary napkins and other absorbent disposable products are envisioned applications for the adhesive composition of the invention, as well as bed pads, absorbing pads, surgical drapes and other related medical or surgical devices. Construction applications, structural applications or packaging applications, in particular disposable items packaging and food packaging, can also be applications where the invention is useful. The most specific application of the present hot melt adhesive is for elastic attachment, wherein the present invention allows bonding of elastic strands on film substrates while applying the adhesive at a temperature lower than 150° C., preferably equal to or lower than 140° C., most preferably lower than 135° C.

Good performance conditions for elastic attachment in a diaper application is typically when the bond retention is either more than 60%, preferably more than 70%, more preferably more than 75%, most preferably more than 80% in a specific test described hereinafter when it is done within 2 days after adhesive has been applied on substrates (initial creep test), or more than 50%, preferably more than 60%, most preferably more than 70%, when it is done after a storage time of one week at 54° C. (one-week-aged creep test). These tests are indicative of what level of adhesion and creep resistance (or bond retention) can be achieved by an adhesive. Because of economics involved in production and in material cost, preferred adhesive add-ons are lower than 18 gsm (grams of adhesive material per square meter of substrate covered by the adhesive material), more preferably equal to or lower than 15 gsm, and most preferably equal to or lower than 12 gsm.

Performances of the adhesive can also be assessed by rheometry, with a temperature sweep in a frequency response analysis configuration to measure loss (G") and storage (G') moduli. Specifically G' at 60° C. and the ratio (called tan delta) of G" over G' at 100° C. area relevant indication of the bond retention under creep conditions of the adhesive bond, and G" at 120° C. and again the ratio (called tan delta) of G" over G' at 100° C. are two parameters that can indicate if the adhesive material can be processed and coated at low temperature, lower than 150° C., preferably equal to or lower than 140° C., most preferably lower than 135° C.

Among tackifying resins conventionally used in hot melt adhesive formulations, the present invention proposes an innovative way to fulfill the earlier described requirements.

Indeed, using high softening point mid-block tackifying resins provides the level of cohesion required to bond elastomeric materials, or to bond materials under mechanical stress and/or under high temperature, while it does not hinder applying the hot melt adhesives at low temperatures. Surprisingly, high softening point (SP) tackifying resins, i.e. an SP equal to or higher than 110° C., preferably equal to or higher than 115° C., can be used in an adhesive that can then be applied with conventional techniques at a temperature lower than 150° C., preferably equal to or lower than 140° C., more preferably lower than 135° C. Depending on the base polymer of the adhesive, the aromatic content of the resin also needs to be defined properly to fulfill the above requirements.

Another aspect of the present invention is the use of low to medium softening point aromatic tackifying resins in conjunction with high softening point mid-block resins. High softening point is defined herein as a softening point equal to or higher than 110° C., preferably equal to or higher than 115° C. Low to medium softening point is defined herein as a softening point below 125° C., preferably between 50 and 120° C., most preferably between 70 and 115° C. Softening point of these aromatic resins is important to control both the molten viscosity at the application temperature and the level of adhesion of the adhesives. It is well known that addition of such aromatic resins affects the Tg of the styrenic phase of a styrene block copolymer (SBc), lowering it or increasing it. However, it has been surprisingly seen in the present invention that this benefit can be expressly useful for both lowering the application temperature of a hot melt adhesive formula and in particular, allowing an application temperature lower than 150° C., preferably equal to or lower than 140° C., most preferably lower than 135° C., and also for getting a high level of bond retention, in conjunction with the use of a mid-block tackifying resin having a softening point high enough for the adhesive bond to withstand mechanical stress like creep effect, potentially at low, ambient or elevated temperature.

Accordingly, the present invention provides a hot melt adhesive composition, comprising a blend of the following components:

about 10% to about 40%, preferably about 10% to about 25%, and most preferably about 12% to about 24%, by weight, of an elastomeric block copolymer having a structure represented by A-B, A-B-A, A-(B-A)$_n$-B, or (A-B)$_n$-Y wherein A comprises a polyvinyl aromatic block having a Tg higher than 80° C., B comprises a rubbery midblock having a Tg lower than −10° C., Y comprises a multivalent compound, and n is an integer of at least 3;

about 15% to about 70%, preferably about 40% to about 65%, and most preferably about 50% to about 62%, by weight, of a first midblock tackifying resin having a softening point of at least about 110° C. and having an aromatic content of at least about 1.5% by weight;

about 0 to 55% of second midblock tackifying resin, about 5% to about 35%, preferably greater than about 14% more preferably greater than about 16% and most preferably greater than about 18%, by weight, of a plasticizer; and about 0% to about 20% by weight of an end block resin having a softening point lower than 125° C.;

wherein the components total 100% by weight of the composition, the viscosity of the composition is equal to or less than about 20,000 mPa·s at 120° C., and is applied at a temperature lower than 150° C., and initial bond retention of the composition on elastic strands is at least about 60%.

Preferably, the block copolymer is selected from SB, SBS, SIS, SIBS, SEBS, SEP, SEPS, SBBS, SEEPS, and blends thereof, and is most preferably SIS, SBS, or a mixture of SIS and SBS block copolymers.

In a particularly preferred embodiment, the viscosity of the hot melt adhesive composition of the present invention is equal to or less than about 20,000 mPa·s at 120° C., and the composition is applied at a temperature lower than 150° C., and the composition has an elastic modulus G' at 60° C. higher than 5000 Pa, preferably higher than 6000 Pa, and a viscous modulus G" at 120° C. higher than about 50 Pa, preferably between 50 Pa and 500 Pa, and a tan delta value at 100° C. between 0.5 and 60, preferably between 1 and 50, more preferably between 2 and 30.

The present invention also provides a laminate comprising a first layer of nonwoven material, a second layer of nonwoven material, and one or a plurality of elastomeric substrates, disposed between said first and second nonwoven layers, bonded together with the adhesive composition.

The laminate may also comprise a first layer of nonwoven material, a second layer of film material, and one or a plurality of elastomeric substrates disposed between said first and second layers, bonded together with the adhesive composition. The film material may comprise a polyethylene film, a polypropylene film, an ethylene-propylene copolymer film or a cloth-like coated film material, and the elastomeric substrate is preferably a plurality of elastic strands.

The laminate may further comprise a first layer of nonwoven material bonded to a second layer of film material with the adhesive composition, and without any elastomeric substrate therebetween.

The adhesive composition and/or laminate of the present invention may be used in making a variety of end products. Examples include a disposable diaper, a sanitary napkin, a bed pad, a bandage, a surgical drape, a tape, a label, a plastic sheet, a nonwoven sheet, a paper sheet, a cardboard, a book, a filter, or a package.

In yet another aspect, the present invention provides a method of making laminate comprising the steps of: feeding a first substrate in a first direction; feeding a second substrate spaced from said first substrate in said first direction; applying the adhesive composition to one or both of said substrates; and composes said substrates together to form the laminate.

When an elastomeric laminate is desired, the method includes the additional steps of feeding one or a plurality of elastomeric substrate or substrates between said first and second substrates in said first direction, said elastomeric substrates are stretched before, during or after adhesive application; and applying the adhesive composition to either said elastomeric substrate or substrates or one or both of said substrates before comprising the substrates together. The elastomeric substrate is preferably a plurality of elastic strands each stretched up to 500% from their initial relaxed state.

DETAILED DESCRIPTION OF THE INVENTION

Figure 1:
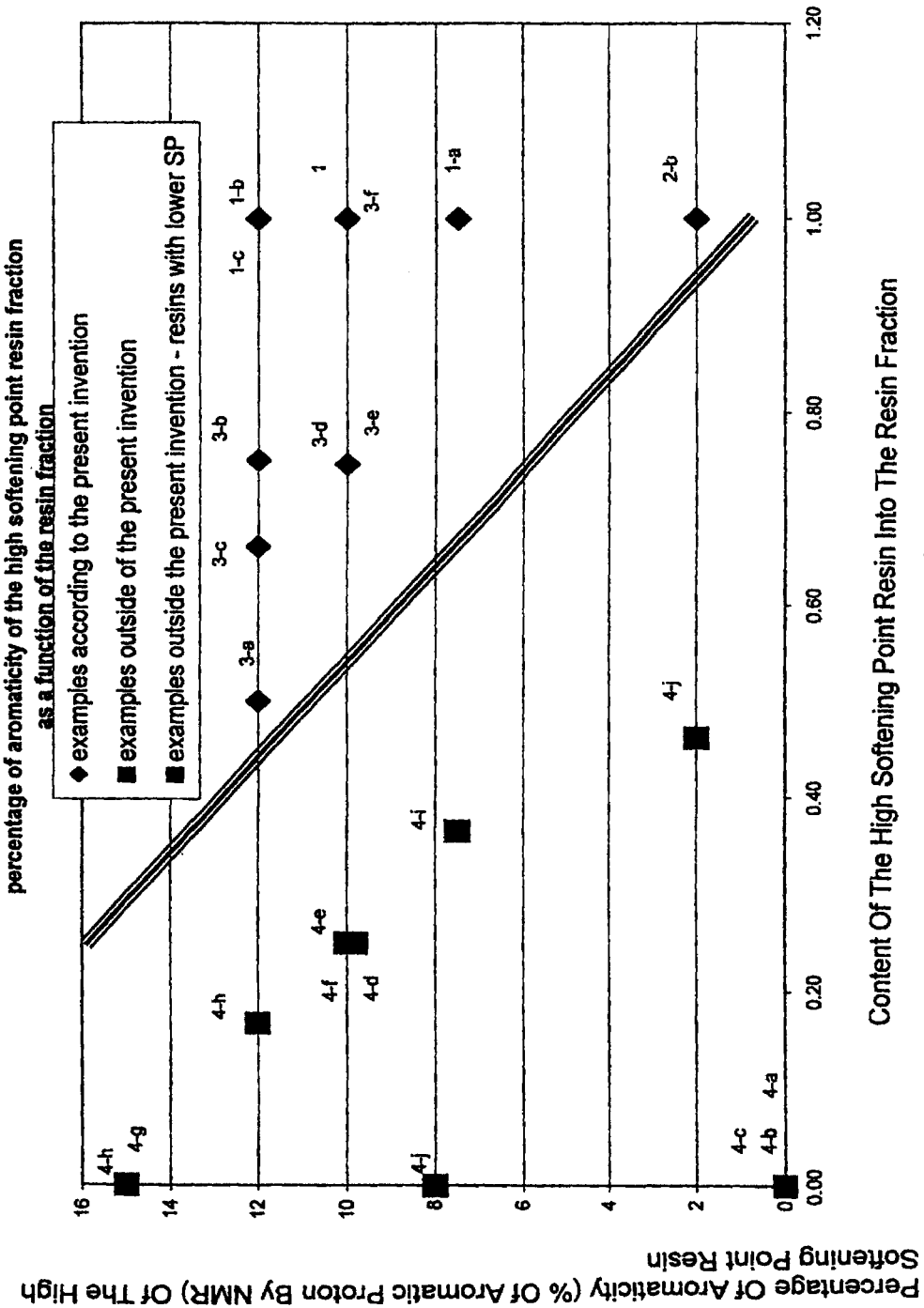
FIG. 1 is a graph illustrating the percentage of aromaticity of the high softening point resin fraction as a function of the high SP resin fraction into the total quantity of tackifying resin.

A tackifying resin, as defined in the present description can be a molecule or a macro-molecule, generally a chemical compound or a fairly low molecular weight polymer, compared to common polymers, from a natural source or from a chemical process or combination thereof that in general enhances the adhesion of a final hot melt adhesive composition. The use of tackifying resins to impart adhesion needs to be assessed by using the same process conditions when applying the adhesive, in order to compare different resins to each other.

Most common tackifying resins are obtained by polymerizing C5 or C9 streams from a petroleum feedstock, or combinations of them together or with other monomers, from natural sources or resulting from any chemical process. Tackifying resins from the C5 streams are called aliphatic resins, while those from the C9 stream or from pure monomers of C9 or C10 configuration or from derivatives or mixtures thereof are called aromatic resins. The C5 stream can be composed of linear or cyclic monomers, or combinations thereof. Also, an aliphatic resin can be obtained by hydrogenation of a polymerized aromatic feedstock. Hydrogenation can also be partial, so that part of the monomers keep their aromatic function into the polymer chain, while some become aliphatic. Any combination can be made in terms of monomer composition and hydrogenation process, in order to have aliphatic or aromatic resins, or to have any incremental point between a substantially aliphatic and a substantially aromatic tackifying resin. Also, an aromatic-modified aliphatic resin is a term that encompasses both cases when some quantity of C9 monomers are polymerized with a major part of C5 monomers, or when a C9 stream is polymerized, then hydrogenated in a way that most of the monomer aromatic functions become aliphatic. Similarly, one would use the term aliphatic-modified aromatic resin when appropriate. Other types of monomers can enter into the composition of such resin's polymeric chain. Resins like terpene-based polymers, for example styrenated terpene resins, are part of the general description referred to herein as hydrocarbon resins, although terpenic monomers are not from petroleum derivatives but from natural sources. Rosin derivatives can be encompassed by the present resin description if one considers their aromatic character measured by a solvent cloud point test method called MMAP that would make them similar or at least comparable to an aromatic modified aliphatic resin. At last, a tackifying resin made substantially out of aromatic monomers can be called an aromatic resin or an end-block resin, as it would be compatible with end-blocks usually made of styrenic or aromatic compounds. Otherwise, the resin would be called a mid-block resin, as compatibility is usually high when the mid-block is made of a rubber aliphatic compound because the mid-block usually composes the main part in weight of the adhesive. In the following description, whenever reference is made to a tackifying resin with no precision about its nature, it would mean a mid-block tackifying resin.

A material's softening point (SP) is defined in the present description by the ring and ball test method ASTM-E 28-99, and aromatic character or aromatic content is defined either by the ratio in percent of hydrogen protons involved in an aromatic bond in the polymer chain, measured by standard $^1$H NMR analytical method, after dissolution for example in deuterium chloroform, or by a solvent cloud point test method called MMAP described in EP 0 802 251 A1. In the cloud point method, the temperature at which turbidity occurs is the cloud point value, when the resin is dissolved in a specific solvent. The lower the cloud point value, the more aromatic character the resin presents, relative to the chemistry of the resin. Usually, the percentage of aromatic protons is less than 0.5% for aliphatic resins, and is usually higher than 40% for aromatic resins. Any resin having an aromatic proton percent between 0.5% and 40% would be called either an aromatic-modified aliphatic tackifying resin or an aliphatic-modified aromatic tackifying resin, and would be considered as a mid-block tackifying resin.

The mid-block tackifying resin ingredient in the present composition may be incorporated entirely from a single resin grade, or may comprise a blend or mixture of two or more resins. The mid-block tackifying resins are preferably selected from aliphatic hydrocarbon resins and their hydrogenated derivatives like Eastotac H-130 available from Eastman Chemical, hydrogenated cycloaliphatic hydrocarbon resins like Escorez 5415 available from Exxon Mobil Chemical, aromatic modified aliphatic or hydrogenated cycloaliphatic resins like Escorez 5615 available from Exxon Mobil Chemical, aliphatic modified aromatic resins like Norsolene M1100 available from Sartomer-Cray Valley, partially or fully hydrogenated aromatic hydrocarbon resins like Regalite S7125 available from Eastman Chemical, polyterpene and styrenated polyterpene resins like Sylvares ZT 115 available from Arizona Chemical. The mid-block tackifying resins are more preferably selected from hydrogenated cycloaliphatic hydrocarbon resins, aromatic modified hydrogenated cycloaliphatic resins, aliphatic modified aromatic resins, partially or fully hydrogenated aromatic hydrocarbon resins, polyterpene and styrenated polyterpene resins. The mid-block tackifying resins are most preferably selected from aromatic modified hydrogenated cycloaliphatic resins, and partially hydrogenated aromatic hydrocarbon resins. The amount of resin used depends on the desired formulation and end use, but should be from about 15% to about 70%, preferably from about 40% to about 65%, and most preferably from about 50% to about 62%, by weight.

Any type of elastomeric block copolymer can be used in a hot melt adhesive formula according to the present invention, and may be incorporated into the composition in amounts of from about 10% to about 40% by weight, preferably from about 10% to about 25% by weight, and most preferably from about 12% to about 24% by weight. Among the useful elastomeric block copolymers are those having structure A-B, A-B-A, A-(B-A)$_n$-B, or (A-B)$_n$-Y wherein A comprises a polyvinyl aromatic block having a Tg higher than 80° C., B comprises a rubbery midblock having a Tg lower than −10° C., Y comprises a multivalent compound, and n is an integer of at least 3. Examples of these latter block copolymers conventionally used in hot melt adhesive compositions are styrenic block copolymers (SBc) and include styrene-butadiene (SB), styrene-butadiene-styrene (SBS), styrene-isoprene-styrene (SIS), styrene-isoprene (SI), styrene-isoprene-butadiene-styrene (SIBS), styrene-ethylene-butylene-styrene (SEBS), styrene-ethylene-butylene (SEB) styrene-ethylene propylene-styrene (SEPS) and styrene-ethylene propylene (SEP) and styrene-ethylene-propylene-styrene (SEEPS or hydrogenated SIBS). While the total styrene content of the polymers can be as much as 51 wt-% of the polymer, and since the polymers can have more than two A blocks for optimal performance, the total A block should be less than or equal to about 45 wt-% of the polymers, and, most preferably, is less than or equal to 35 wt-% of the polymer. In an S-B-S (styrene-butadience-styrene) copolymer, the preferred molecule weight is about 50,000 to 120,000, and the preferred styrene content is about 20 to 45 wt-%. In an S-I-S (styrene-isoprene-styrene) copolymer, the preferred molecular weight is about 100,000 to 200,000 and the preferred styrene content is about 14-35 wt-%. Hydrogenating the butadiene midblocks produces rubbery midblocks that are typically converted to ethylene-butylene midblocks. Such block copolymers are available for example from Kraton Polymers, Polimeri Europa, Total Petrochemicals, Dexco, and Kuraray. Multiblock or tapered block copolymers (the A-(B-A)$_n$-B type) are available from Firestone. Block copolymers structures can contain any acrylic monomers or acrylic phase in general, either presenting a high Tg like methyl methacrylate, or having an elastomeric behavior like butyl acrylate. Also, the polymer fraction of the hot melt adhesive can contain one or more other phases, can contain more than one structure or can contain other polymers like copolymers of ethene, propene or other olefinic monomer, or like copolymerization of acrylic monomers. These additional polymers can be homopolymers, or copolymers and can be potentially modified by any during- or after-polymerization modification like grafting or chain-scission. Blends of various polymers may also be employed so long as the composition retains the desired viscosity, creep resistance and low temperature application characteristics of the present invention.

Hot melt adhesive formulas according to the present invention also contain about 5% to about 35%, preferably about 14% to about 35%, more preferably about 16% to about 35%, and most preferably about 18% to about 35%, by weight, of any plasticizer. A suitable plasticizer may be selected from the group which not only includes the usual plasticizing oils, such as mineral oil, but also olefin oligomers and low molecular weight polymers, glycol benzoates, as well as vegetable and animal oil and derivatives of such oils. The petroleum-derived oils that may be employed are relatively high boiling temperature materials containing only a minor proportion of aromatic hydrocarbons. In this regard, the aromatic hydrocarbons should preferably be less than 30%, and more particularly less than 15%, by weight, of the oil. Alternately, the oil may be totally non-aromatic. The oligomers may be polypropylenes, polybutenes, hydrogenated polyisoprene, hydrogenated butadiene, or the like having average molecular weights between about 100 and about 10,000 g/mol. Suitable vegetable and animal oils include glycerol esters of the usual fatty acids and polymerization products thereof. Other plasticizers may be used provided they have suitable compatibility. Nyflex 222B, a naphtenic mineral oil manufactured by Nynas Corporation, has also been found to be an appropriate plasticizer. As will be appreciated, plasticizers have typically been employed to lower the viscosity of the overall adhesive composition without substantially decreasing the adhesive strength and/or the service temperature of the adhesive. The choice of plasticizer can be useful in formulation for specific end uses (such as wet strength core applications). Because of economics involved in production and in material cost, as plasticizers are usually of lower cost than other materials involved in the formulation like polymers and tackifying resins, the amount of plasticizer in the adhesive should be about 5% to about 35% by weight, preferably higher than about 14% in weight, more preferably higher than about 16%, and most preferably higher than about 18%.

Waxes can also be used in the adhesive composition, and are used to reduce the melt viscosity of the hot melt construction adhesives without appreciably decreasing their adhesive bonding characteristics. These waxes also are used to reduce the open time of the composition without affecting the temperature performance.

The wax material component of the adhesive is optional but when included may comprise up to about 25% by weight of the adhesive composition.

Among the useful wax materials are:

(1) Low molecular weight, that is, 100-6000 g/mol, polyethylene having a hardness value, as determined by ASTM method D-1321, of from about 0.1 to 120 and ASTM softening points of from about 66° C.° to 120° C.;

(2) Petroleum waxes such as paraffin wax having a melting point of from about 130° to 170° F. and microcrystalline wax having a melting point of from about 135° to 200° F., the latter melting points being determined by ASTM method D127-60;

(3) atactic polypropylene having a Ring and Ball softening point of from about 120° to 160° C.;

(4) metallocene catalyzed propylene-based wax like those commercialized by Clariant under the name "Licocene".

(5) metallocene catalyzed wax or single-site catalyzed wax like for example those described in U.S. Pat. Nos. 4,914,253, 6,319,979 or WO 97/33921 or WO 98/03603.

(6) synthetic waxes made by polymerizing carbon monoxide and hydrogen such as Fischer-Tropsch wax; and (7) polyolefin waxes. As used herein, the term "polyolefin wax" refers to those polymeric or long-chain entities comprised of olefinic monomer units. These materials are commercially available from Eastman Chemical Co. under the trade name "Epolene." The materials which are preferred to use in the compositions of the present invention have a Ring and Ball softening point of 200° F. to 350° F. As should be understood, each of these waxes is solid at room temperature. Other useful substances include hydrogenated animal, fish and vegetable fats and oils such as hydrogenated tallow, lard, soy oil, cottonseed oil, castor oil, menhadin oil, cod liver oil, etc., and which are solid at ambient temperature by virtue of their being hydrogenated, have also been found to be useful with respect to functioning as a wax material equivalent.

These hydrogenated materials are often referred to in the adhesives industry as "animal or vegetable waxes".

The preferred wax material is a paraffin wax having a melting point of 60° C. to 70° C., a hard wax such as Paraflint H1 commercialized by Sasol-Schuman, or Bareco PX 100 commercialized by Bareco, those hard waxes having a hardness dmm at 23° C. of about 2 dmm or less and a melting point of 75° C. to 120° C., or blends of a paraffin wax and a hard wax. The preferred hard wax has a melting point lower than 95° C. The term "hard wax" refers to any low molecular weight, highly crystalline ethylene-based polymer.

The adhesive also typically includes a stabilizer or antioxidant. The stabilizers which are useful in the hot melt adhesive compositions of the present invention are incorporated to help protect the polymers noted above, and thereby the total adhesive system, from the effects of thermal and oxidative degradation which normally occurs during the manufacture and application of the adhesive as well as in the ordinary exposure of the final product to the ambient environment. Such degradation is usually manifested by a deterioration in the appearance, physical properties and performance characteristics of the adhesive. A particularly preferred antioxidant is Irganox 1010, a tetrakis(methylene(3,5-di-teri-butyl-4-hydroxyhydrocinnamate))methane manufactured by Ciba-Geigy. Among the applicable stabilizers are high molecular weight hindered phenols and multifunctional phenols, such as sulfur and phosphorus-containing phenols. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group serves to retard its stretching frequency and correspondingly, its reactivity; this steric hindrance thus providing the phenolic compound with its stabilizing properties. Representative hindered phenols include:

1,3,5-trimethyl-2,4,6-tris(3,5-di-tert-butyl-4-hydroxybenzyl) benzene;
pentaerythritol tetrakis-3(3,5-di-tert-butyl-4-hydroxyphenyl) propionate;
n-octadecyl-3(3,5-ditert-butyl-4-hydroxyphenyl) propionate;
4,4'-methylenebis(4-methyl-6-tert butylphenol);
4,4'-thiobis(6-tert-butyl-o-cresol);
2,6-di-tert-butylphenol;
6-(4-hydroxyphenoxy)-2,4-bis(n-ocytlthio)-1,3,5-triazine;
2,4,6-tris(4-hydroxy-3,5-di-tert-butyl-phenoxy)-1,3,5-triazine;
di-n-octadecyl-3,5-di-tert-butyl-4-hydroxybenzylphosphonate;
2-(n-octylthio)ethyl-3,5-di-tert-butyl-4-hydroxybenzoate; and
sorbitol hexa-(3,3,5-di-tert-butyl-4-hydroxy-phenyl) propionate.

The performance of these stabilizers may be further enhanced by utilizing, in conjunction therewith; (1) synergists such as, for example, as thiodipropionate esters and phosphites; and (2) chelating agents and metal deactivators as, for example, ethylenediaminetetraacetic acid, salts thereof, and disalicyalpropylenediimine.

The adhesive composition useful in the method of the present invention may be produced using any of the techniques known in the art. A representative example of the procedure involves placing all of the substances, in a jacketed mixing kettle, and preferably in a jacketed heavy duty mixer of the Baker-Perkins or Day type, and which is equipped with rotors, and thereafter raising the temperature of this mixture to a range of 120° C. to 177° C. It should be understood that the precise temperature to be used in this step would depend on the melting point of the particular ingredients. The resulting adhesive composition is agitated until the polymers completely dissolve. A vacuum is then applied to remove any entrapped air.

Optional additives may be incorporated into the adhesive composition in order to modify particular physical properties. These additives may include colorants, such as titanium dioxide and fillers such as talc and clay, crosslinking agents, nucleating agents, reactive compounds, fire-retardant mineral or organic agents, as well as ultraviolet light (UV) absorbing agents and UV fluorescing agents.

Among the existing tackifying resins, a preference is made in the present invention for polymerized ones, as the balance between aromatic and aliphatic character is easier to get from choosing monomers or adjusting hydrogenation process conditions. The softening point value is also easier to determine by adjusting the length of the resin's polymeric chain once the monomers have been selected.

In the adhesive of the present invention, tackifying resins that have softening points equal or higher than 110° C., preferably equal to or higher than 115° C., should be incorporated into the formulation. At least part of the total tackifying resin amount incorporated into the formulation should have this level of softening point. This high softening point tackifying resin fraction can be comprised of one resin grade, or a blend/combination of different resins.

In SIS-based hot melt adhesives, the high softening point resin fraction should also have a minimum level of aromaticity, to allow the adhesive to fulfill all the requirements in term of processability and adhesion performances. The minimum of aromaticity needed is 1.5%, preferably 2% of the protons to be of aromatic nature. In a more preferred option, this minimum should be correlated to the actual amount of the resin fraction which has a SP above 110° C. This correlation may be expressed by the following formula:

$$y \geq -17x+18$$

where y is the aromaticity content in % of aromatic protons, and where x is the resin fraction of softening point equal to or greater than 110° C., preferably equal to or 115° C. For example, the resin fraction (having a softening point of at least 110° C.) that would be 10% aromatic should represent at least 0.5 of the total mid-block tackifying resin quantity in the adhesive, according to the present invention.

Whenever one would use a rosin derived tackifying resin, MMAP cloud point method should be used to characterize it, and compare it to the MMAP value of partially hydrogenated aromatic hydrocarbon tackifying resins, so that one can give a theoretical but relevant aromaticity content of this rosin deviated resin that should be considered for the correlation cited above. In any case, the aromaticity content of the highest softening point resin (softening point higher than 110° C.) should be equal or higher than about 1%, preferably higher than 1.5%, more preferably higher than 2%.

Simultaneously, in SIS-based adhesives, the high softening point resin fraction should have a softening point high enough to withstand mechanical stress under a wide range of temperature, especially elevated temperature due to weather conditions. It has been found that the adhesive should contain a resin with a softening point equal to or above 110° C., preferably 115° C., and more preferably the softening point should follow the correlation:

$$z \geq -60x+146$$

where z is the actual softening point of the resin fraction which softening point is above 110° C., preferably equal to or above 115° C., and where x is the resin fraction of softening point equal to or greater than 110° C., preferably equal to or greater than 115° C.

For example, the resin fraction that would have a softening point of 120° C. should represent at least 0.44 of the total mid-block tackifying resin quantity in the adhesive, according to the present invention.

Figure 2:
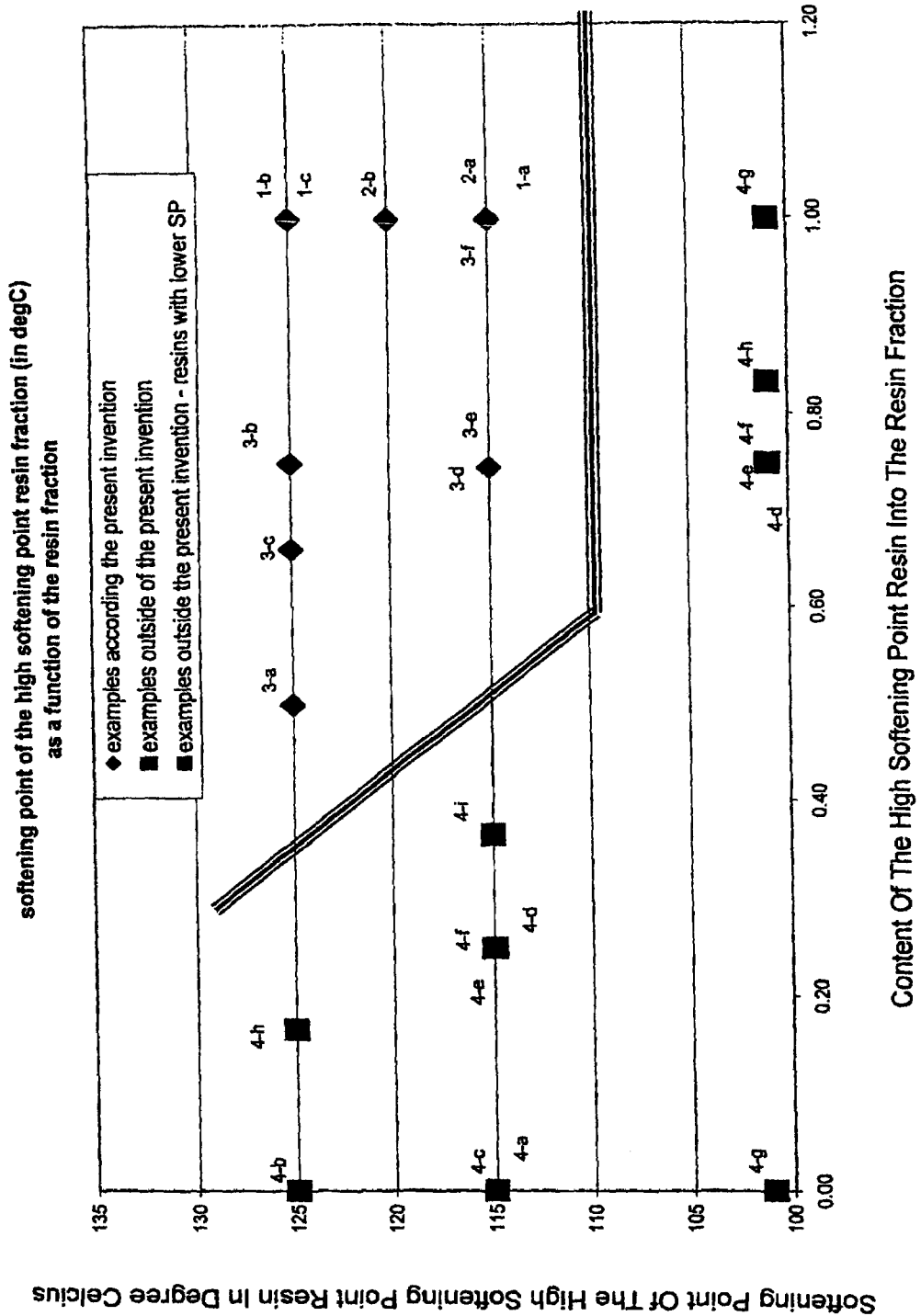
FIG. 2 is a graph illustrating the softening point of the high softening point resin fraction as a function of the high SP resin fraction into the total quantity of tackifying resin.

For SIS-based adhesives, in the graph FIG. 2, the softening point of the highest softening point resin should be higher than 110° C., preferably higher than 115° C., and more preferably should correspond to points in FIG. 2 that are in the right upper corner defined by the two straight lines, i.e. about and to the right of the lines.

For SIS-based adhesives, in the graph FIG. 1, the aromaticity content of the highest softening point resin should be equal or higher than about 1%, preferably equal or higher than 2%, and preferably be defined by points in FIG. 1 that are to the right side of the straight line.

It should be noted that the data points plotted in FIGS. 1 and 2 represent adhesive compositions in the Examples herein. In other words, for example, in FIG. 1 the data point labeled 3-c is the adhesive composition of Example 3 which composition is shown in Table 3a.

In SBS-containing adhesives, the tackifying resin in the adhesive should have a softening point high enough to withstand mechanical stress under a wide range of temperature, especially elevated temperature due to weather conditions during shipping and storage periods. At least a fraction of the resin total quantity should have a softening point high enough to fulfill these requirements. It has been found that adhesion performances can be achieved when at least 0.5 of the resin fraction has a softening point equal to or higher than 110° C., preferably equal to or higher than 115° C.

In another embodiment, the adhesive formula may contain a sufficiently low softening point substantially fully aromatic resin. The aromatic or substantially fully aromatic resin should have softening point equal to or below 125° C., preferably equal to or below 115° C., and more preferably equal to or below 100° C. Preferably, this substantially fully aromatic resin will be made of pure monomer polymerization of styrene, alpha-methyl styrene, toluene, indene monomers or similar monomers, or derivatives, or mixtures thereof. Preferably, styrene and/or alpha-methyl-styrene and/or vinyl-toluene monomers are among the monomer composition of the pure monomer resin. Quantity of this resin should be under 20% in the adhesive composition, preferably between 2% to 15%, more preferably 4% to 12%, and most preferably 6% to 10%. Specifically for this embodiment of the present invention, the highest softening point mid-block resin should be at least 25% of the tackifying resin fraction, and the this highest SP should be equal or higher than 110° C., preferably equal or higher than 115° C.

Various methods are conventionally used to coat a hot melt adhesive at fairly low viscosity on a substrate. This can be made by roll coating or any printing type method, or by slot coating, by extrusion or by spray gun. Spray gun techniques are numerous and can be done with or without assistance of compressed air that would shape the adhesive spray, and consequently the adhesive pattern. The hot melt adhesive material is generally allowed to melt in tanks, and then pumped through hoses to the final coating spot on the substrates.

For the present invention, preferred methods of applying the adhesive would be by spray application, most preferably assisted by air. Among these techniques, the most common are spiral spray (Controlled Fiberization™ by Nordson), Summit™ by Nordson, Surewrap™ by Nordson, Omega™ by ITW, Curtain Coating™ by Nordson and melt blown process. For the present invention, the temperature at which the hot melt adhesive is applied should be below 150° C., so that the heat sensitive substrates will not be damaged. Preferably, this temperature should be equal to or lower than 140° C., most preferably lower than 135° C.

The viscosity of the adhesive material needs to be generally lower than 20,000 mPa·s, more preferably lower than 15,000 mPa·s, most preferably lower than 12,000 mPa·s at the application temperature in order to achieve the right pattern and consequently the right bonding performances. Line speed, add-on levels as well as open time, set time, compression forces and compression time are also process control parameters.

Taking the example of bonding elastic strands in the environment of a diaper manufacturing process, typical conditions are very stringent regarding the adhesive features. The adhesive is typically sprayed either on a polymeric film (usually ethylene based or propylene based under 40 gsm of basis weight), or on elastic strands stretched at up to about 500% from their initial relaxed state, and preferably at about 300% elongation. Film and elastic strands are put in contact together, before, during or after the adhesive spray. The film together with the stretched elastic strands are then laminated to a non-woven web of low basis weight (under 50 gsm). In fact, the primary substrate can also be a non-woven web, and can be the same as the secondary web substrate, when this web is simply sprayed with adhesive and then folded over the elastic strands. Plastic films can have various features like breathability, color, printing, stretchiness, embossing, or surface treatments, for example to favor adhesion from adhesives or inks. Elastic strands can be made of natural or synthetic rubber, of specialty polyurethane formulations, and can be in a strip form, or in a multifilament form. More specifically elastic strands for diaper construction are usually made of polyester polyurethane microfilaments bonded together to get the right elastomeric strength, like Lycra™ or Lycra XA™ from Invista, or narrow bands made of natural or synthetic rubber narrow bands like Fullflex™, from Fulflex Elastomerics.

Line speeds can be as high as 700 feet per minute or higher, open times are typically around 0.2 second, and can be considered to be the same as compression time. Set time is considered as immediate or negligible, as compression into nip rolls is usually helping the adhesive material to set. Add-on levels vary according to applications and to the required level of bond strength, from a few gsm of adhesive, on a localized area where the elastic strands need to be bonded. The viscosity of the adhesives of the present invention is lower than 20,000 mPa·s at 120° C. Preferably, it should be lower than 15,000 mPa·s, more preferably below 12,000 mPa·s, as determined by employing a Brookfield Thermocel or other appropriate viscometer and utilizing the testing techniques which are set forth in ASTM Method D3236-73.

The present invention thus encompasses any process of conventional or non-conventional elastic attachment technology as known in the state of the art. The present invention also encompasses any application where various materials can be involved like non-woven materials, polymeric films, and in general elastomeric components put in items like diapers, in a form of strands, films, nonwovens or any other continuous or discrete form. Any substrate material and any substrate form could be used in any combination possible, the adhesive allowing to bond two or more substrates together. Form of substrates can be for example fiber, film, thread, strip, ribbon, coating, foil, sheet, and band. Material of substrate can be a polyolefin, a polyacrylic, a polyester, a polyvinyl chloride, a polystyrene, a cellulosic like wood, cardboard and paper, or made out of a mineral compound like concrete, glass or ceramics. The substrate mechanical behavior can be rigid, plastic or elastomeric. Among elastomeric materials are various examples like natural or synthetic rubber, polyurethane based copolymers, polyether or polyester urethanes, block copolymers of styrene or of amides, or olefinic copolymers. The above list is not limitative, but is only meant to describe examples of what the present invention may encompass.

Also, in the present invention, various methods to process hot melt adhesives can be envisioned, linked to their ability to be melted, and transported and/or coated or sprayed in a molten stage to the final location where the bond is required.

The present invention encompasses any application where laminates, composites and disposable products are made with the help of bonding parts together with a hot melt adhesive used at a temperature lower than 150° C., preferably equal to or lower than 140° C., most preferably lower than 135° C., while obtaining good cohesion from the adhesive bond to withstand mechanical stress at low, ambient or elevated temperature, in particular under creep conditions. Diaper, adult incontinence products, sanitary napkins and other absorbent disposable products can be envisioned applications for the invention, as well as bed pads, absorbing pads, surgical drapes and other related medical or surgical devices. Construction applications, structural applications or packaging applications, in particular disposable items packaging and food packaging can be applications where the invention is useful. Specifically for elastic attachment, the present invention allows bonding of the elastic strands on film substrates while applying the adhesive at a temperature lower than 150° C., preferably equal to or lower than 140° C., most preferably lower than 135° C. Bonding strength is measured primarily by testing the bond under a specific creep configuration, giving a model of the constraints encountered in a real life cycle of a disposable diaper, where baby movements are stretching the laminates at room temperature or body temperature. Creep test methods can vary among the industry, and the Applicant has developed over the years its own test method that satisfies the majority of the applications seen in the field, and, more important, that can compare and differentiate adhesives from each other, determining if one adhesive is suitable or not for an efficient elastic attachment function, once this adhesive has been coated to form a laminated structure. The creep test can be performed within the first days following the coating operation, and can be performed after a few days or few weeks at elevated temperature, to simulate the effects of ageing under storage and shipping conditions.

Conditions evidencing good performance for elastic attachment in a diaper application is typically when the initial bond retention is either more than 60%, preferably more than 70%, more preferably more than 75%, most preferably more than 80% when the creep test is performed within 2 days after adhesive has been applied on substrates (initial creep test), or more than 50%, preferably more than 60%, most preferably more than 70%, when it is done after a storage time of one week at 54° C. (one-week-aged creep test). These conditions are indicative of what level of adhesion and bond retention under creep conditions can be achieved. These conditions depend on the adhesive application technique used, like spiral spray or surewrap for example; on the level of adhesive add-on; on process parameters like air pressure, line speed, and adhesive temperature. Because of economics involved in production and in material cost, preferred adhesive add-ons are lower than 18 gsm, more preferably equal to or lower than 15 gsm, most preferably equal to or lower than 12 gsm.

Performance of the adhesive can also be assessed by rheometry, with a single temperature sweep in a vibratory mode configuration to measure loss (G") and storage (G') moduli. Specifically G' at 60° C. and the ratio (called tan delta) of G" over G' at 100° C. are a relevant indication of the bond retention of the adhesive, and G" at 120° C. and again the ratio (called tan delta) of G" over G' at 100° C. are two parameters that can indicate if the adhesive material can be processed and coated at low temperature, i.e. lower than 150° C., preferably equal to or lower than 140° C., most preferably lower than 135° C.

A good performance adhesive, for both processability, cohesion and adhesion, should have an elastic modulus G' at 60° C. higher than 5000 Pa, preferably higher than 6000 Pa, and a viscous modulus G" at 120° C. higher than 50 Pa, preferably between 50 and 500 Pa, as well as a tan delta value at 100° C. of between 0.5 and 60, preferably between 1 and 50, more preferably between 2 and 30.

Hot melt adhesive compositions can be easily characterized directly by different conventional analytical methods or after solubilization and/or semi-preparative liquid chromatography followed by a fraction-by-fraction identification, such as Gel Permeation Chromatography, High Pressure Liquid Chromatography, Differential Scanning Calorimetry (DSC), Infra-Red (bulk or surface) spectroscopy, steric exclusion chromatography, TREF i.e. crystallinity-driven fractional SEC, Nuclear Magnetic Resonance (NMR).

If a hot melt adhesive composition is applied on a heat sensitive substrate, the heat deterioration of this substrate will depend on the adhesive quantity as well as the adhesive temperature among other parameters. It is easy to recognize if a substrate material is intrinsically heat sensible, using for example DSC technique. If such a heat sensitive substrate seen in the field has not been damaged by the hot melt adhesive application, this should mean that this application has been done at a relatively low temperature, related to whatever melting point, softening point or degradation temperature the substrate material would exhibit. This is a way to try to recognize a posteriori if a hot melt adhesive has been applied at relatively low temperature or not.

EXAMPLES

Hot melt adhesive were prepared with the ingredients and mixing procedures described herein below. A total of 2000 grams each were made and the mixing was carried out at about 150° C. to 190° C. under carbon dioxide atmosphere in a laboratory type mixer that consists of a propeller powered by a motor, a heating mantle, a temperature control unit and a container of about 1 gallon in size. The appropriate amounts of each component, calculated according to the ratios shown in the tables below, were added to the container in an appropriate sequence to allow mixing while limiting the heat or shear degradation of ingredients. After the ingredients in the container were completely melted and mixed thoroughly to allow a good visual homogeneity, samples were stored appropriately to be tested.

Laminated specimens were formed by using a Nordson Meltex CT225, or Nordson NT4015 hot melt high speed coater, at 800 feet per minute. When a spiral spray technique was used, the coater was fitted with a conventional 0.018-inch to 0.020-inch diameter spiral spray extrusion nozzle, with 12 air holes, available from Nordson Corporation. When Surewrap technique was used, the coater was fitted with a 3-strands 0.018 inch diameter extrusion nozzle available from Nordson Corporation. Adhesives were sprayed at various coating weights, depending on the application required, with different open times—typically 0.05 to 0.1 seconds—to the 1-bar-nip rolls compression. Application temperature was set between 120° C. and 130° C., or higher temperatures for some counter-examples.

Standard polypropylene-based spun-bond non-woven web is available from BBA Corporation at 15.7 gram per square meter coating weight. Standard polyethylene non-breathable treated and embossed white film at 17 gram per square meter is available under trade name DH-216 from Clopay Corporation. Standard spandex strands are available from Invista, under the Trademark Lycra XA, and the grade used is 262P, at 800 decitex.

When spiral spray is used, the spray head is generally perpendicular to the substrate and at a height between 0.5 and 1 inch to get a 12 to 14 mm wide pattern into the laminated structure, covering 3 parallel strands of Lycra material with 5 mm in-between them. Usually between 5 and 8 to 10 spiral revolution shapes per linear inch can be counted, depending on process parameters and on the adhesive composition and viscosity. The term flat configuration is used when the adhesive is sprayed over the elastic strands and the first film substrate touching each other, and the term wrap configuration is used when the adhesive is sprayed into the elastic strands, and wraps around them, before the elastic strands come into contact with the first film substrate. The wrap configuration gets a better surface coverage of the elastic strands than the flat one and thus will give in general a better creep test result.

When Surewrap technology is used, the required pattern is visually assessed, as we try to recognize along the adhesive filament the number of thick beads per linear inch, usually around 5 beads or more. The measure of pressure in the compressed air system is dependant on the circuit form and length, as well as on the spot the measurement is made. Usually 10 to 20 to 25 psi is recorded for either Surewrap or spiral spray. Air temperature is usually between 0 and 14 to 28° C. higher than the adhesive temperature.

Creep Resistance or bond retention test is carried out with the laminated specimens containing elastic strands. The specimen, cut to about 300 mm in length, is stretched out completely and its ends were securely attached to a piece of rigid board. A length of 200 mm was marked in the machine direction and the elastic strands are cut at the marks. The specimen is then placed in an air-circulating oven at 100° F. Under these conditions, the stretched elastic strands can retract or contract to a certain distance. The distance between the ends of each elastic strand is measured after four hours. The ratio of the final length to the initial length, defined as bond Retention and expressed in percentage (%), is a measure of the ability of the adhesive to hold the elastic strands. This ratio is measured on 8 to 12 elastic strands and the result is then averaged. If this test is performed within 2 days after the adhesive coating has been done, it is called the initial creep test. If it is performed after the specimen have been put in an oven at 60° C. one week after the coating operation, this test is called the one-week-aged creep test.

Performances of the adhesive can also be assessed by rheometry, with a temperature sweep in a frequency response analysis configuration to measure loss (G") and storage (G') moduli. The frequency is kept at 10 rad/s, the strain rate is imposed to an adhesive sample, adapted to the measurement conditions for torque and displacement and compatible with the Newtonian domain of the adhesive material, and the level of G' and G" are recorded every 4° C. from 140° C. till −50° C. on a sample maintained in-between two parallel temperature-controlled metal plates. Specifically G' at 60° C. and the ratio (called tan delta) of G" over G' at 100° C. and G" at 120° C. are reported.

Following raw materials have been used in the various compositions shown in examples:

NYFLEX 222B is a naphthenic oil available from Nynas Corporation.

ARKON M-115 and M-100 are partially hydrogenated aromatic tackifying resins with a softening point of respectively about 115° C. and about 100° C., available from Arakawa Chemical.

SUKOREZ SU-420 is a hydrogenated polycyclic aromatic-modified aliphatic tackifying resin with a softening point of about 120° C., available from Kolon Chemical.

REGALITE S-5100 and S-7125 are partially hydrogenated aromatic tackifying resins with softening points of respectively about 100° C. and about 125° C., available from Eastman Chemical.

NORSOLENE M-1091 is an aliphatic-modified aromatic tackifying resin with a softening point of about 105° C., available from Cray Valley.

ESCOREZ 5400 and 5415 are both hydrogenated polycyclic aliphatic tackifying resins with softening points respectively of about 100° C. and about 115° C., available from Exxon Mobil Chemicals.

ESCOREZ 5600 and 5615 are both hydrogenated polycyclic aromatic-modified aliphatic tackifying resins with softening points respectively of about 100° C. and about 115° C., available from Exxon Mobil Chemicals.

PICCOTEX 75 and 120, KRISTALEX 3070 and 3085 and F115 are pure monomer fully aromatic tackifying resins with softening points of about respectively 75° C., 120° C., 70° C., 85° C. and 115° C., available from Eastman Chemical.

VECTOR 4211, 4215 and 4411 and DPX-602 are SIS block-copolymers available from Dexco.

VECTOR 4461 is an SBS block-copolymer available from Dexco.

EUROPRENE SOL T6414 and SOL T9326 are respectively SBS and SIS block-copolymers available from Polymeri Europe.

KRATON D-1124 is an SIS block copolymer available from Kraton Polymers.

IRGANOX 1010 is a hindered phenol type of antioxidant obtained from Ciba-Specialty Chemicals, Tarryton, N.Y.

H2465-03 is a commercial hot melt adhesive for elastic attachment applications when applied at around 154° C., available from Bostik, Inc.

The invention is further illustrated by way of the specific examples that are set forth below.

Example 1

Table 1a illustrates three different compositions suitable according to the present invention, containing three different polymers, with viscosity at 120° C., and values of G' and G" in specific conditions. Table 1b illustrates the initial creep resistance results of the compositions described in Table 1a when coated at 125° C. to 130° C., when the adhesive add-on is 12 and 15 gsm, in flat or wrap spray configuration. Table 1c shows the one-week-aged creep test results. From these results, it is clear that the three formulas are suitable to fulfill the requirements the present invention has described.

Example 2

Table 2a illustrates four different compositions suitable according to the present invention, containing three different resins, with viscosity at 120° C., and values of G' and G" in specific conditions. Table 2b illustrates the initial creep test results of the compositions described in Table 2a when coated at various temperatures from 120° C. to 130° C., when the adhesive add-on is 12 and 15 gsm, in flat or wrap spray configuration. Table 2c shows the one-week-aged creep test results. From these results, it is clear that the four formulas are suitable to fulfill the requirements the present invention has described.

Example 3

Table 3a illustrates six different compositions suitable according to the present invention, containing six different tackifying resin fractions where only part are high softening point aromatic-modified tackifying resin grades, with viscosity at 120° C., and values of G' and G" in specific conditions. Table 3b illustrates the initial creep test results of the compositions described in Table 3a when coated at various temperatures from 125° C. to 130° C., when the adhesive add-on is 12 and 15 gsm, in flat or wrap spray configuration. Table 3c shows the one-week-aged creep test results. From these results, it is clear that the six formulas are suitable to fulfill the requirements the present invention has described.

Example 4

Tables 4a illustrates ten different compositions that are not suitable according to the present invention, with viscosity at 120° C., and values of G' and G" in specific conditions. Table 4b illustrates the initial creep test results of the compositions described in Table 4a, when the adhesive add-on is 12 and 15 gsm and when coated at various temperatures from 120° C. to 130° C., in flat or wrap spray configuration. Table 4c shows the one-week-aged creep test results. From these results, it is clear that none of these ten formulas is suitable to fullfill the requirements the present invention has described, either because the viscosity was far too high to be applied at low temperature, or because of the poor results obtained in the creep tests.

Example 5

Table 5a illustrates one composition outside of the formulation domain claimed by the present invention, H2465-03, but that could work at higher temperature, with its viscosity value at 120° C. Table 5b illustrates the initial creep test results of the composition described in Table 5a, when the adhesive add-on is 12 and 15 gsm when coated at 154° C., in flat or wrap spray configuration. Table 5c shows the one-week-aged creep test results. This kind of commercial adhesive has been applied in the market place at temperatures around 150° C. and above. Applying them at lower temperature, when their viscosity level allows it, induces a significant lack of wet-out from the adhesive material onto the substrates' surfaces, leading then to poor bond retention.

Example 6

Table 6a illustrates two different compositions suitable according to the present invention, containing different resins or polymers with viscosity at 120° C., and values of G' and G" in specific conditions. Table 6b illustrates the initial creep test results of the compositions described in Table 6a when coated at various temperatures from 120° C. to 130° C., when the adhesive add-on is 15 gsm, in flat or wrap spray configuration. Table 6c shows the one-week-aged creep test results. From these results, it is clear that the two formulas are suitable to fulfill the requirements the present invention has described.

Example 7

Table 7a illustrates four different compositions suitable according to the present invention, containing an SBS polymer, with viscosity at 120° C., and values of G' and G" in specific conditions. Table 7b illustrates the initial creep test results of the compositions described in Table 7a when coated at various temperatures from 125° C. to 130° C., when the adhesive add-on is 15 gsm, in flat or wrap spray configuration. Table 7c shows the one-week-aged creep test results. From these results, it is clear that the four formulas are suitable to fulfill the requirements the present invention has described.

Example 8

Table 8a illustrates two different compositions suitable according to the present invention, containing a mixture of SIS and SBS polymers, with viscosity at 120° C., and values of G' and G" in specific conditions. Table 8b illustrates the initial creep test results of the compositions described in Table 8a when coated at various temperatures from 125° C. to 130° C., when the adhesive add-on is 15 gsm, in flat or wrap spray configuration. Table 8c shows the one-week-aged creep test results. From these results, it is clear that the two formulas are suitable to fulfill the requirements the present invention has described.

Example 9

Table 9a illustrates two different compositions suitable according to the present invention, with viscosity at 120° C., and values of G' and G" in specific conditions. Table 9b illustrates the initial creep test results of the compositions described in Table 9a when coated at various temperatures from 120° C. to 130° C., when the adhesive add-on is 33 and 45 mg per linear meter of each elastic strand, in Surewrap™ technique configuration. Table 9c shows the one-week-aged creep test results. From these results, it is clear that the two formulas are suitable to fulfill the requirements the present invention has described.

TABLE 1a composition, physical properties

| | Sample name | | |
|---|---|---|---|
| | 1-a | 1-b | 1-c |
| Composition | | | |
| Nyplast 222B | 22 | 23 | 22 |
| Arkon M115 | 59.6 | | |
| Regalite S7125 | | 59.1 | 59.6 |
| Vector 4211 | 17.9 | | |
| Vector 4215 | | 17.4 | |
| Vector 4411 | | | 17.9 |
| Irganox 1010 | 0.5 | 0.5 | 0.5 |
| Physical properties | | | |
| Brookfield viscosity @ 120° C. (mPa · s) | 8940 | 15850 | 20250 |
| G' @ 60° C. (Pa) | 5300 | 8050 | 6500 |
| G" @ 120° C. (Pa) | 62 | 103 | 70 |
| tanδ @ 100° C. | 15 | 5.2 | 13 |

TABLE 1b creep resistance results, initial test.

| Application temperature (° C.) | Add-on and pattern | Sample name 1-a | 1-b | 1-c |
|---|---|---|---|---|
| | | Bond retention (%) | | |
| 125 | 12 gsm flat spiral | | 57 | |
| 125 | 12 gsm wrapped spiral | | 62 | |
| 125 | 15 gsm flat spiral | | 70 | |
| 125 | 15 gsm wrapped spiral | 64 | 77 | 73 |
| 130 | 12 gsm flat spiral | | 70 | |
| 130 | 12 gsm wrapped spiral | | 75 | |
| 130 | 15 gsm flat spiral | | 83 | |
| 130 | 15 gsm wrapped spiral | 58 | 86 | 76 |

TABLE 1c creep resistance results, 1 week aging.

| Application temperature (° C.) | Add-on and pattern | Sample name 1-a | 1-b | 1-c |
|---|---|---|---|---|
| | | Bond retention (%) | | |
| 125 | 12 gsm flat spiral | | | |
| 125 | 12 gsm wrapped spiral | | 55 | |
| 125 | 15 gsm flat spiral | | | |
| 125 | 15 gsm wrapped spiral | | 65 | |
| 130 | 12 gsm flat spiral | | 55 | |
| 130 | 12 gsm wrapped spiral | | 56 | |
| 130 | 15 gsm flat spiral | | 59 | |
| 130 | 15 gsm wrapped spiral | | 78 | |

TABLE 2a composition, physical properties

| | Sample name | | | |
|---|---|---|---|---|
| | 1-a | 1-b | 2-a | 2-b |
| Composition | | | | |
| Nyplast 222B | 22 | 23 | 23 | 23 |
| Arkon M115 | 59.6 | | | |
| Regalite S7125 | | 59.1 | | |
| Escorez 5615 | | | 59.1 | |
| Sukorez SU420 | | | | 59.1 |
| Vector 4211 | 17.9 | | | |
| Vector 4215 | | 17.4 | 17.4 | 17.4 |
| Irganox 1010 | 0.5 | 0.5 | 0.5 | 0.5 |
| Physical properties | | | | |
| Brookfield viscosity @ 120° C. (mPa·s) | 8940 | 15850 | 9912 | 11020 |
| G' @ 60° C. (Pa) | 5300 | 8050 | 7500 | 10200 |
| G" @ 120° C. (Pa) | 62 | 103 | 86 | 1040 |
| tanδ @ 100° C. | 15 | 5.2 | 17 | 51 |

TABLE 2b creep resistance results, initial test.

| Application temperature (° C.) | Add-on and pattern | Sample name 1-a | 1-b | 2-a | 2-b |
|---|---|---|---|---|---|
| | | Bond retention (%) | | | |
| 120 | 15 gsm wrapped spiral | | | | 71 |
| 125 | 12 gsm flat spiral | | 57 | | 55 |
| 125 | 12 gsm wrapped spiral | | 62 | | 57 |
| 125 | 15 gsm flat spiral | | 70 | | 59 |
| 125 | 15 gsm wrapped spiral | 64 | 77 | 69 | 65 |
| 130 | 12 gsm flat spiral | | 70 | | |
| 130 | 12 gsm wrapped spiral | | 75 | | |
| 130 | 15 gsm flat spiral | | 83 | | |
| 130 | 15 gsm wrapped spiral | 58 | 86 | | |

TABLE 2c creep resistance results, 1 week aging

| Application temperature (° C.) | Add-on and pattern | Sample name 1-a | 1-b | 2-a | 2-b |
|---|---|---|---|---|---|
| | | Bond retention (%) | | | |
| 120 | 15 gsm wrapped spiral | | | 55 | |
| 125 | 12 gsm flat spiral | | | | 44 |
| 125 | 12 gsm wrapped spiral | | 55 | | 46 |
| 125 | 15 gsm flat spiral | | | | 44 |
| 125 | 15 gsm wrapped spiral | | 65 | 58 | 48 |
| 130 | 12 gsm flat spiral | | 55 | | |
| 130 | 12 gsm wrapped spiral | | 56 | | |
| 130 | 15 gsm flat spiral | | 59 | | |
| 130 | 15 gsm wrapped spiral | | 78 | | |

TABLE 3a composition, physical properties

| | Sample name | | | | | |
|---|---|---|---|---|---|---|
| | 3-a | 3-b | 3-c | 3-d | 3-e | 3-f |
| Composition | | | | | | |
| Nyplast 222B | 22 | 22 | 23 | 23 | 23 | 21.8 |
| Regalite S7125 | 29.8 | 44.7 | 39.1 | | | |
| Escorez 5615 | | | | 44 | 44 | 58.1 |
| Norsolene M1091 | | | 20 | | | |
| Regalite S5100 | | | | | 15.1 | |
| Escorez 5600 | 29.8 | 14.9 | | 15.1 | | |
| Vector 4215 | 17.9 | 17.9 | 17.4 | 17.4 | 17.4 | |
| Vector 4411 | | | | | | 20.1 |
| Irganox 1010 | 0.5 | 0.5 | 0.5 | 0.5 | 0.5 | 0.5 |
| Physical properties | | | | | | |
| Brookfield viscosity @ 120° C. (mPa·s) | 13230 | 15470 | 9725 | 10300 | 9600 | 9290 |
| G' @ 60° C. (Pa) | 7121 | 9200 | 7100 | 6800 | 6200 | 14836 |
| G" @ 120° C. (Pa) | 175 | 103 | 85 | 95 | 84 | 90 |
| tanδ @ 100° C. | 24 | 7.7 | 15 | 17 | 12 | 19 |

TABLE 3B creep resistance results, initial test.

| Application temperature (°C.) | Add-on and pattern | 3-a | 3-b | 3-c | 3-d | 3-e | 3-f |
|---|---|---|---|---|---|---|---|
| | | | | Bond retention (%) | | | |
| 125 | 12 gsm flat spiral | | | | | | |
| 125 | 12 gsm wrapped spiral | | 65 | 62 | 62 | 64 | |
| 125 | 15 gsm flat spiral | | | | | | 58 |
| 125 | 15 gsm wrapped spiral | 70 | 75 | | | | 70 |
| 130 | 12 gsm flat spiral | | | | | | |
| 130 | 12 gsm wrapped spiral | | 64 | | | | |
| 130 | 15 gsm flat spiral | | | | | | |
| 130 | 15 gsm wrapped spiral | 76 | 85 | | | | |

TABLE 3c creep resistance results, 1 week aging

| Application temperature (°C.) | Add-on and pattern | 3-a | 3-b | 3-c | 3-d | 3-e | 3-f |
|---|---|---|---|---|---|---|---|
| | | | | Bond retention (%) | | | |
| 125 | 12 gsm flat spiral | | | | | | |
| 125 | 12 gsm wrapped spiral | | 59 | | | | |
| 125 | 15 gsm flat spiral | | | | | | 51 |
| 125 | 15 gsm wrapped spiral | | 65 | | | | 62 |
| 130 | 12 gsm flat spiral | | | | | | |
| 130 | 12 gsm wrapped spiral | | 59 | | | | |
| 130 | 15 gsm flat spiral | | | | | | |
| 130 | 15 gsm wrapped spiral | | 70 | | | | |

TABLE 4a composition, physical properties

| | 4-a | 4-b | 4-c | 4-d | 4-e | 4-f | 4-g | 4-h | 4-i | 4-j |
|---|---|---|---|---|---|---|---|---|---|---|
| Composition | | | | | | | | | | |
| Nyplast 222B | 21 | 23 | 23.0 | 23.5 | 23.5 | 23.5 | 23.5 | 23.5 | 22 | 23 |
| Arkon M115 | | | | | | | | | 21.8 | |
| Sukorez SU420 | | | | | | | | | | 27.3 |
| Regalite S7125 | | | | | | | | | | |
| Regalite R1125 | | 59.1 | | | | | | | | |
| Escorez 5615 | | | | 15.1 | 15 | 15 | | | | |
| Escorez 5415 | 61.6 | | 59.1 | | | | | | | |
| Regalite S5100 | | | | 45 | 45 | 45 | 60 | 50.0 | | |
| Arkon M-100 | | | | | | | | | 37.8 | |
| Escorez 5600 | | | | | | | | | | 31.8 |
| Vector 4211 | | | | | | | | | 17.9 | |
| Vector 4215 | 16.9 | 17.4 | 17.4 | | 16 | | | | | 17.4 |
| Vector 4411 | | | | | | 16 | | | | |
| Vector DPX593 | | | | 15.9 | | | 16 | 16.0 | | |
| Irganox 1010 | 0.5 | 0.5 | 0.5 | 0.5 | 0.5 | 0.5 | 0.5 | 0.5 | 0.5 | 0.5 |
| Physical properties | | | | | | | | | | |
| Brookfield viscosity @ 120° C. (mPa·s) | 21400 | 96370 | 32400 | 6237 | 5700 | 3100 | 5700 | 4710 | 6430 | 8200 |
| G' @ 60° C. (Pa) | 7300 | | | 4550 | 4400 | 3700 | 3400 | 4700 | 4600 | 8600 |
| G'' @ 120° C. (Pa) | 177 | | 35 | 38 | 27 | 41 | 35 | 30 | | 780 |
| tanδ @ 100° C. | 2 | | 21 | 22 | 17 | 24 | 18 | 15 | | 70 |

TABLE 4b creep resistance results, initial test.

| Application temperature (°C.) | Add-on and pattern | 4-a | 4-b | 4-c | 4-d | 4-e | 4-f | 4-g | 4-h | 4-i | 4-j |
|---|---|---|---|---|---|---|---|---|---|---|---|
| | | | | | | Bond retention (%) | | | | | |
| 120 | 12 gsm flat spiral | | | | 31 | 41 | 38 | 39 | 40 | | |
| 120 | 12 gsm wrapped spiral | | | | 33 | 46 | 35 | 42 | 42 | | |
| 120 | 15 gsm flat spiral | | | | | | | | | 45 | |
| 120 | 15 gsm wrapped spiral | | | | | | | | | 48 | |
| 125 | 12 gsm flat spiral | | | | 32 | 46 | 35 | 46 | 39 | | 45 |
| 125 | 12 gsm wrapped spiral | | | | 37 | 49 | 42 | | 45 | | 43 |
| 125 | 15 gsm flat spiral | | | | | | | 49 | 42 | 45 | 47 |
| 125 | 15 gsm wrapped spiral | | | | | | | 52 | 50 | 52 | 48 |
| 130 | 12 gsm flat spiral | | | | 32 | 45 | 40 | 41 | | | 48 |
| 130 | 12 gsm wrapped spiral | | | | | | | | | | 50 |
| 130 | 15 gsm flat spiral | | | | | | | | | 45 | |
| 130 | 15 gsm wrapped spiral | | | | | | | | | | 44 |

TABLE 4c creep resistance results, 1 week aging

| Application temperature (° C.) | Add-on and pattern | 4-a | 4-b | 4-c | 4-d | 4-e | 4-f | 4-g | 4-h | 4-i | 4-j |
|---|---|---|---|---|---|---|---|---|---|---|---|
| | | Sample name / Bond retention (%) | | | | | | | | | |
| 125 | 12 gsm flat spiral | | | | | | | | | | 37 |
| 125 | 12 gsm wrapped spiral | | | | | | | | | | 41 |
| 125 | 15 gsm flat spiral | | | | | | | | | | 38 |
| 125 | 15 gsm wrapped spiral | | | | | | | | | | 42 |
| 130 | 12 gsm flat spiral | | | | | | | | | | 39 |
| 130 | 12 gsm wrapped spiral | | | | | | | | | | 42 |
| 130 | 15 gsm flat spiral | | | | | | | | | | |
| 130 | 15 gsm wrapped spiral | | | | | | | | | | |

TABLE 5a composition, physical properties

| Physical properties | Sample name H2465-03 |
|---|---|
| Brookfield viscosity @ 120° C. (mPa·s) | 12000 |

TABLE 5b creep resistance results, initial test.

| Application temperature (° C.) | Add-on and pattern | Sample name H2465-03 Bond retention (%) |
|---|---|---|
| 155 | 12 gsm flat spiral | 62 |
| 155 | 12 gsm wrapped spiral | 67 |
| 155 | 15 gsm flat spiral | 74 |
| 155 | 15 gsm wrapped spiral | 76 |

TABLE 5c creep resistance results, 1 week aging.

| Application temperature (° C.) | Add-on and pattern | Sample name H2465-03 Bond retention (%) |
|---|---|---|
| 155 | 12 gsm flat spiral | 55 |
| 155 | 12 gsm wrapped spiral | 63 |
| 155 | 15 gsm flat spiral | 67 |
| 155 | 15 gsm wrapped spiral | 70 |

TABLE 6a composition, physical properties

| | Sample name | |
|---|---|---|
| | 6-a | 6-b |
| Composition | | |
| Nyplast 222B | 18.9 | 22.1 |
| Regalite S7125 | 20.6 | 19.3 |
| Escorez 5415 | 20.6 | 19.3 |
| Escorez 5600 | 15.9 | 14.9 |
| Piccotex 75 | | 8.0 |
| Kristalex 3085 | 8.4 | |
| Vector 4215 | 15.1 | |
| Vector DPX593 | | 16.0 |
| Irganox 1010 | 0.5 | |
| Physical properties | | |
| Brookfield viscosity @ 120° C. (mPa·s) | 10400 | 7010 |
| G' @ 60° C. (Pa) | 8770 | 7640 |
| G" @ 120° C. (Pa) | 100 | 280 |
| tanδ @ 100° C. | 13.5 | 19 |

TABLE 6b creep resistance results, initial test.

| Application temperature (° C.) | Add-on and pattern | 6-a | 6-b |
|---|---|---|---|
| | | Bond retention (%) | |
| 120 | 12 gsm flat spiral | 69 | 62 |
| 120 | 12 gsm wrapped spiral | 64 | |
| 120 | 15 gsm flat spiral | | 62 |
| 120 | 15 gsm wrapped spiral | | 69 |
| 125 | 12 gsm flat spiral | | |
| 125 | 12 gsm wrapped spiral | | |
| 125 | 15 gsm flat spiral | 73 | |
| 125 | 15 gsm wrapped spiral | 84 | |
| 130 | 12 gsm flat spiral | 73 | |
| 130 | 12 gsm wrapped spiral | | |
| 130 | 15 gsm flat spiral | | |
| 130 | 15 gsm wrapped spiral | | |

TABLE 6c creep resistance results, 1 week aging.

| Application temperature (° C.) | Add-on and pattern | 6-a | 6-b |
|---|---|---|---|
| | | Bond retention (%) | |
| 120 | 12 gsm flat spiral | 62 | 53 |
| 120 | 12 gsm wrapped spiral | 61 | |
| 120 | 15 gsm flat spiral | | 54 |
| 120 | 15 gsm wrapped spiral | | 57 |
| 125 | 12 gsm flat spiral | | |
| 125 | 12 gsm wrapped spiral | | |

TABLE 6c-continued creep resistance results, 1 week aging.

| Application temperature (° C.) | Add-on and pattern | Sample name 6-a | 6-b |
|---|---|---|---|
| | | Bond retention (%) | |
| 125 | 15 gsm flat spiral | 63 | |
| 125 | 15 gsm wrapped spiral | 75 | |

TABLE 7a composition, physical properties

| | Sample name | | | |
|---|---|---|---|---|
| | 7-a | 7-b | 7-c | 7-d |
| Composition | | | | |
| Nyplast 222B | 22 | 22 | 20.9 | 20.9 |
| Arkon M115 | 59.6 | | | |
| Escorez 5615 | | | 28.9 | 28.7 |
| Escorez 5415 | | 59.6 | | |
| Arkon M100 | | | 28.6 | 28.6 |
| Vector 4461D | 17.9 | 17.9 | | |
| Europrene Sol T 6414 | | | 21.6 | 10.9 |
| Europrene Sol T 9326 | | | | 10.9 |
| Irganox 1010 | 0.5 | 0.5 | 0.5 | 0.5 |
| Physical properties | | | | |
| Brookfield viscosity @ 120° C. (mPa · s) | 10640 | 10675 | 16021 | 13780 |
| G' @ 60° C. (Pa) | 10730 | 18470 | 17934 | 14403 |
| G" @ 120° C. (Pa) | 86 | 90 | 142 | 126 |
| tanδ @ 100° C. | 29 | 5.2 | 26 | 25 |

TABLE 7b creep resistance results, initial test.

| Application temperature (° C.) | Add-on and pattern | Sample name 7-a | 7-b | 7-c | 7-d |
|---|---|---|---|---|---|
| | | Bond retention (%) | | | |
| 125 | 12 gsm flat spiral | | | | |
| 125 | 12 gsm wrapped spiral | | | | |
| 125 | 15 gsm flat spiral | | | | |
| 125 | 15 gsm wrapped spiral | 70 | 65 | | |
| 130 | 12 gsm flat spiral | | | | |
| 130 | 12 gsm wrapped spiral | | | | |
| 130 | 15 gsm flat spiral | | | 70 | 68 |
| 130 | 15 gsm wrapped spiral | | | 76 | 74 | 70 |

TABLE 7c creep resistance results, 1 week aging

| Application temperature (° C.) | Add-on and pattern | Sample name 7-a | 7-b | 7-c | 7-d |
|---|---|---|---|---|---|
| | | Bond retention (%) | | | |
| 125 | 12 gsm flat spiral | | | | |
| 125 | 12 gsm wrapped spiral | | | | |
| 125 | 15 gsm flat spiral | | | | |
| 125 | 15 gsm wrapped spiral | | | | |
| 130 | 12 gsm flat spiral | | | | |

TABLE 7c-continued creep resistance results, 1 week aging

| Application temperature (° C.) | Add-on and pattern | Sample name 7-a | 7-b | 7-c | 7-d |
|---|---|---|---|---|---|
| | | Bond retention (%) | | | |
| 130 | 12 gsm wrapped spiral | | | | |
| 130 | 15 gsm flat spiral | | | 57 | 61 |
| 130 | 15 gsm wrapped spiral | | | 55 | 60 |

TABLE 8a composition, physical properties

| | Sample name | |
|---|---|---|
| | 8-a | 8-b |
| Composition | | |
| Nyplast 222B | 22.5 | 21.7 |
| Regalite S7125 | 19.6 | 18.9 |
| Escorez 5415 | 19.6 | 18.9 |
| Escorez 5600 | 15.2 | 14.7 |
| Piccotex 120 | | 7.7 |
| Piccotex 75 | 8.0 | 3.7 |
| Finaprene 602 D | 7.2 | 6.9 |
| Vector DPX593 | 7.2 | 6.9 |
| Irganox 1010 | 0.5 | 0.5 |
| Physical properties | | |
| Brookfield viscosity @ 120° C. (mPa · s) | 6812 | 6775 |
| G' @ 60° C. (Pa) | 8390 | 8500 |
| G" @ 120° C. (Pa) | 650 | 720 |
| tanδ @ 100° C. | 22 | 17 |

TABLE 8b creep resistance results, initial test.

| Application temperature (° C.) | Add-on and pattern | Sample name 8-a | 8-b |
|---|---|---|---|
| | | Bond retention (%) | |
| 120 | 12 gsm flat spiral | | |
| 120 | 12 gsm wrapped spiral | | 73 |
| 120 | 15 gsm flat spiral | | |
| 120 | 15 gsm wrapped spiral | | |
| 125 | 12 gsm flat spiral | | |
| 125 | 12 gsm wrapped spiral | | |
| 125 | 15 gsm flat spiral | 53 | 58 |
| 125 | 15 gsm wrapped spiral | 72 | 76 |

TABLE 8c creep resistance results, 1 week aging.

| Application temperature (° C.) | Add-on and pattern | Sample name 8-a | 8-b |
|---|---|---|---|
| | | Bond retention (%) | |
| 120 | 12 gsm flat spiral | | |
| 120 | 12 gsm wrapped spiral | | 53 |
| 120 | 15 gsm flat spiral | | |
| 120 | 15 gsm wrapped spiral | | |
| 125 | 12 gsm flat spiral | | |
| 125 | 12 gsm wrapped spiral | | |

TABLE 8c-continued creep resistance results, 1 week aging.

| Application temperature (° C.) | Add-on and pattern | Sample name 8-a | 8-b |
|---|---|---|---|
| | | Bond retention (%) | |
| 125 | 15 gsm flat spiral | | 50 |
| 125 | 15 gsm wrapped spiral | 65.0 | 53 |

TABLE 9a composition, physical properties

| | Sample name | |
|---|---|---|
| | 2-a | 9-b |
| Composition | | |
| Nyplast 222B | 23 | 18.9 |
| Regalite S7125 | | 20.6 |
| Escorez 5615 | 59.1 | |
| Escorez 5415 | | 20.6 |
| Escorez 5600 | | 15.9 |
| Kristalex 3085 | | 8.4 |
| Vector 4215 | 17.4 | |
| Vector DPX593 | | 15.1 |
| Irganox 1010 | 0.5 | 0.5 |
| Physical properties | | |
| Brookfield viscosity @ 120° C. (mPa · s) | 9912 | 8970 |
| G' @ 60° C. (Pa) | 7500 | 8900 |
| G" @ 120° C. (Pa) | 86 | 115 |
| tanδ @ 100° C. | 17 | 15 |

TABLE 9b creep resistance results, initial test.

| Application temperature (° C.) | Add-on and pattern | Sample name 2-a | 9-b |
|---|---|---|---|
| | | Bond retention (%) | |
| 120 | Surewrap ™ 33 mg/lm/strand | | 72 |
| 125 | Surewrap ™ 45 mg/lm/strand | 71 | |
| 130 | Surewrap ™ 45 mg/lm/strand | 80 | |

TABLE 9c creep resistance results, 1 week aging.

| Application temperature (° C.) | Add-on and pattern | Sample name 2-a | 9-b |
|---|---|---|---|
| | | Bond retention (%) | |
| 120 | Surewrap ™ 33 mg/lm/strand | | 57 |
| 125 | Surewrap ™ 45 mg/lm/strand | 56 | |
| 130 | Surewrap ™ 45 mg/lm/strand | 66 | |

The invention claimed is:

1. A hot melt adhesive composition, comprising a blend of the following components:
 about 10% to about 40% by weight of an elastomeric block copolymer having a structure represented by A-B, A-B-A, A-(B-A)$_n$-B, or (A-B)$_n$-Y wherein A comprises a polyvinyl aromatic block having a Tg higher than 80° C., B comprises a rubbery midblock having a Tg lower than −10° C., Y comprises a multivalent compound, and n is an integer of at least 3, wherein said block copolymer is a mixture of SIS and SBS block copolymers;
 about 15% to about 70% by weight of a first midblock tackifying resin having a softening point of at least about 110° C. and having an aromatic content of at least about 1.5% by weight;
 about 0 to 55% of second midblock tackifying resin
 about 5% to about 35% by weight of a plasticizer; and
 about 0% to about 20% by weight of an end block tackifying resin having a softening point lower than 125° C.;
 wherein the components total 100% by weight of the composition, the viscosity of the composition is equal to or less than about 20,000 mPa·s at 120° C., and may be applied at a temperature lower than 150° C. and initial bond retention of the composition on elastic strands is at least about 60%.

2. The composition of claim 1 wherein said mixture of SIS and SBS block copolymers further includes a block copolymer which is selected from the group consisting of SB, SIBS, SEBS, SEP, SEPS, SBBS, SEEPS and blends thereof.

3. The composition of claim 2 wherein said block copolymer has a styrene content of from about 20% to about 51% by weight.

4. The composition of claim 1 wherein said first midblock resin has a softening point of at least about 115° C.

5. The composition of claim 1 wherein said first midblock resin has an aromatic content of at least about 2% by weight 6. The composition of claim 1 wherein a fraction x of said total midblock resin has a softening point z of at least about 115° C., so that $z \geq -60x+146$, and has an aromaticity content y so that $y \geq -17x+18$.

7. The composition of claim 1 wherein said composition has a viscosity equal to or less than 15,000 mPa·s at 120° C.

8. The composition of claim 1 wherein said composition has a viscosity equal to or less than 12,000 mPa·s at 120° C.

9. The composition of claim 1 wherein the end-block tackifying resin is a product from pure monomer polymerization.

10. The composition of claim 1 wherein the end-block tackifying resin has a softening point of from 50 to 120° C.

11. The composition of claim 1 wherein the end-block tackifying resin has a softening point of from 70 to 115° C.

12. The composition of claim 1 having about 40% to about 65% by weight of said first midblock tackifying resin.

13. The composition of claim 1 having about 50% to about 62% by weight of said first midblock tackifying resin.

14. The composition of claim 1 wherein said composition has an initial bond retention of at least about 70%.

15. The composition of claim 1 wherein said composition has an initial bond retention of at least about 75%.

16. The composition of claim 1 wherein said composition has an initial bond retention of at least about 80%.

17. The composition of claim 1 further having a one-week-aged bond retention of at least about 50%.

18. The composition of claim 1 further having a one-week-aged bond retention of at least about 60%.

19. The composition of claim 1 further having a one-week-aged bond retention of at least about 70%.

20. The composition of claim 1 wherein the midblock tackifying resin has an aromaticity content of at least 1.5% by weight and is selected from the group consisting of aliphatic hydrocarbon resins and their hydrogenated derivatives, hydrogenated cycloaliphatic hydrocarbon resins, aromatic modified aliphatic or hydrogenated cycloaliphatic hydrocarbon resins, aliphatic modified aromatic hydrocarbon resins, partially or fully hydrogenated aromatic hydrocarbon resins, polyterpene and styrenated polyterpene resins.

21. The composition of claim 1 further including a plasticizer is selected from the group consisting of mineral oil and liquid polybutene.

22. The composition of claim 1 wherein further including a wax is selected from the group consisting of petroleum waxes, microcrystalline waxes, low molecular weight polyethylene and polypropylene, synthetic waxes and polyolefin waxes.

23. A hot melt adhesive composition, comprising a blend of the following components:
   about 10% to about 40% by weight of an elastomeric block copolymer having a structure represented by A-B, A-B-A, A-(B-A)$_n$-B, or (A-B)$_n$-Y wherein A comprises a polyvinyl aromatic block having a Tg higher than 80° C., B comprises a rubbery midblock having a Tg lower than −10° C., Y comprises a multivalent compound, and n is an integer of at least 3 wherein said block copolymer is a mixture of SIS and SBS block copolymers;
   about 15% to about 70% by weight of a first midblock tackifying resin having a softening point of at least about 110° C. and having an aromatic content of at least about 1.5% by weight;
   about 0 to 55% of second midblock tackifying resin;
   about 5% to about 35% by weight of a plasticizer; and
   about 0% to about 20% by weight of an end block tackifying resin having a softening point lower than 125° C.;
   wherein the components total 100% by weight of the composition, the viscosity of the composition is equal to or less than about 20,000 mPa·s at 120° C., and may be applied at a temperature lower than 150° C., and the elastic modulus G' at 60° C. is higher than about 5000 Pa, and the viscous modulus G" at 120° C. is higher than about 50 Pa, and the tan delta value at 100° C. is between about 0.5 and about 60.

24. The composition of claim 23 wherein said elastic modulus G' is higher than about 6000 Pa.

25. The composition of claim 23 wherein said viscous modulus G" is between about 50 Pa and about 500 Pa.

26. The composition of claim 23 wherein said tan delta value is between about 1 and about 50.

27. The composition of claim 23 wherein said tan delta value is between about 2 and about 30.

28. The composition of claim 23 wherein said mixture of SIS and SBS block copolymers further includes a block copolymer which is selected from the group consisting of SB, SIBS, SEBS, SEP, SEPS, SBBS, SEEPS and blends thereof.

29. The composition of claim 23 wherein said block copolymer has a styrene content of from about 20% to about 51% by weight.

30. The composition of claim 23 wherein said first midblock resin has a softening point of at least about 115° C.

31. The composition of claim 23 wherein said first midblock resin has an aromatic content of at least about 2% by weight.

32. The composition of claim 23 wherein a fraction x of said total midblock resin has a softening point z of at least about 115° C., so that z≧−60x+146, and has an aromaticity content y so that y≧−17x+18.

33. The composition of claim 23 wherein said composition has a viscosity equal to or less than 15,000 mPa·s at 120° C.

34. The composition of claim 23 wherein said composition has a viscosity equal to or less than 12,000 mPa·s at 120° C.

35. The composition of claim 23 wherein the end-block tackifying resin is a product from pure monomer polymerization.

36. The composition of claim 23 wherein the end-block tackifying resin has a softening point of from 50 to 120° C.

37. The composition of claim 23 wherein the end-block tackifying resin has a softening point of from 70 to 115° C.

38. The composition of claim 23 having about 40% to about 65% by weight of said first midblock tackifying resin.

39. The composition of claim 23 having about 50% to about 62% by weight of said first midblock tackifying resin.

40. The composition of claim 23 wherein the midblock tackifying resin has an aromaticity content of at least 1.5% by weight and is selected from the group consisting of aliphatic hydrocarbon resins and their hydrogenated derivatives, hydrogenated cycloaliphatic hydrocarbon resins, aromatic modified aliphatic or hydrogenated cycloaliphatic hydrocarbon resins, aliphatic modified aromatic hydrocarbon resins, partially or fully hydrogenated aromatic hydrocarbon resins, polyterpene and styrenated polyterpene resins.

41. The composition of claim 23 further including a plasticizer is selected from the group consisting of mineral oil and liquid polybutene.

42. The composition of claim 23 wherein further including a wax is selected from the group consisting of petroleum waxes, microcrystalline waxes, low molecular weight polyethylene and polypropylene, synthetic waxes and polyolefin waxes.

43. A hot melt adhesive composition, comprising a blend of the following components:
   about 10% to about 25% by weight of an elastomeric block copolymer having a structure represented by A-B, A-B-A, A-(B-A)$_n$-B, or (A-B)$_n$-Y wherein A comprises a polyvinyl aromatic block having a Tg higher than 80° C., B comprises a rubbery midblock having a Tg lower than −10° C., Y comprises a multivalent compound, and n is an integer of at least 3, and wherein said block copolymer is an SIS block copolymer having a styrene content of about 14% to about 35% by weight;
   about 40% to about 65% by weight of a first midblock tackifying resin having a softening point of about 110° C. to about 125° C. and having an aromatic content of at least about 1.5% by weight;
   about 0 to 55% of second midblock tackifying resin
   about 14% to about 35% by weight of a liquid plasticizer; and
   about 0% to about 20% by weight of an end block tackifying resin having a softening point lower than 125° C.;
   wherein the components total 100% by weight of the composition, said composition having an elastic modulus G' at 60° C. higher than about 5000 Pa, and a viscous modulus G" at 120° C. higher than about 50 Pa, and a tan delta value at 100° C. between about 0.5 and about 60; the viscosity of the composition is equal to or less than about 20,000 mPa·s at 120° C., and may be applied by spraying at a temperature lower than 150° C. and initial bond retention of the composition on elastic strands is at least about 60%.

44. The composition of claim 43 wherein said block copolymer further includes a block copolymer which is selected from the group consisting of SB, SBS, SIBS, SEBS, SEP, SEPS, SBBS, SEEPS and blends thereof.

45. The composition of claim 43 wherein said first midblock resin has a softening point of at least about 115° C.

46. The composition of claim 43 wherein said first midblock resin has an aromatic content of at least about 2% by weight.

47. The composition of claim 43 wherein a fraction x of said total midblock resin has a softening point z of at least about 115° C., so that z≧−60x+146, and has an aromaticity content y so that y≧−17x+18.

48. The composition of claim 43 wherein said composition has a viscosity equal to or less than 15,000 mPa·s at 120° C.

49. The composition of claim 43 wherein said composition has a viscosity equal to or less than 12,000 mPa·s at 120° C.

50. The composition of claim 43 wherein the end-block tackifying resin is a product from pure monomer polymerization.

51. The composition of claim 43 wherein the end-block tackifying resin has a softening point of from 50 to 120° C.

52. The composition of claim 43 wherein the end-block tackifying resin has a softening point of from 70 to 115° C.

53. The composition of claim 43 having about 50% to about 62% by weight of said first midblock tackifying resin.

54. The composition of claim 43 wherein said composition has an initial bond retention of at least about 70%.

55. The composition of claim 43 wherein said composition has an initial bond retention of at least about 75%.

56. The composition of claim 43 wherein said composition has an initial bond retention of at least about 80%.

57. The composition of claim 43 further having a one-week-aged bond retention of at least about 50%.

58. The composition of claim 43 further having a one-week-aged bond retention of at least about 60%.

59. The composition of claim 43 further having a one-week-aged bond retention of at least about 70%.

60. The composition of claim 43 wherein the midblock tackifying resin has an aromaticity content of at least 1.5% by weight and is selected from the group consisting of aliphatic hydrocarbon resins and their hydrogenated derivatives, hydrogenated cycloaliphatic hydrocarbon resins, aromatic modified aliphatic or hydrogenated cycloaliphatic hydrocarbon resins, aliphatic modified aromatic hydrocarbon resins, partially or fully hydrogenated aromatic hydrocarbon resins, polyterpene and styrenated polyterpene resins.

61. The composition of claim 43 further including a plasticizer is selected from the group consisting of mineral oil and liquid polybutene.

62. The composition of claim 43 wherein further including a wax is selected from the group consisting of petroleum waxes, microcrystalline waxes, low molecular weight polyethylene and polypropylene, synthetic waxes and polyolefin waxes.

63. The composition of claim 43 wherein said elastic modulus G' is higher than about 6000 Pa.

64. The composition of claim 43 wherein said viscous modulus G" is between about 50 Pa and about 500 Pa.

65. The composition of claim 43 wherein said tan delta value is between about 1 and about 50.

66. The composition of claim 43 wherein said tan delta value is between about 2 and about 30.

67. A hot melt adhesive composition, comprising a blend of the following components:
about 10% to about 25% by weight of an elastomeric block copolymer having a structure represented by A-B, A-B-A, A-(B-A)$_n$-B, or (A-B)$_n$-Y wherein A comprises a polyvinyl aromatic block having a Tg higher than 80° C., B comprises a rubbery midblock having a Tg lower than −10° C., Y comprises a multivalent compound, and n is an integer of at least 3, and wherein said block copolymer is an SBS block copolymer having a styrene content of about 20% to about 45% by weight;
about 40% to about 65% by weight of a first midblock tackifying resin having a softening point of about 110° C. to about 125° C. and having an aromatic content of at least about 1.5% by weight;
about 0 to 55% of second midblock tackifying resin about 14% to about 35% by weight of a liquid plasticizer; and
about 0% to about 20% by weight of an end block tackifying resin having a softening point lower than 125° C.;
wherein the components total 100% by weight of the composition, said composition having an elastic modulus G' at 60° C. higher than about 5000 Pa, and a viscous modulus G" at 120° C. higher than about 50 Pa, and a tan delta value at 100° C. between about 0.5 and about 60; the viscosity of the composition is equal to or less than about 20,000 mPa·s at 120° C., and may be applied by spraying at a temperature lower than 150° C. and initial bond retention of the composition on elastic strands is at least about 60%.

68. The composition of claim 67 wherein said block copolymer further includes a block copolymer which is selected from the group consisting of SB, SIS, SIBS, SEBS, SEP, SEPS, SBBS, SEEPS and blends thereof.

69. The composition of claim 67 wherein said first midblock resin has a softening point of at least about 115° C.

70. The composition of claim 67 wherein said first midblock resin has an aromatic content of at least about 2% by weight.

71. The composition of claim 67 wherein a fraction x of said total midblock resin has a softening point z of at least about 115° C., so that $z \geq -60x+146$, and has an aromaticity content y so that $y \geq -17x+18$.

72. The composition of claim 67 wherein said composition has a viscosity equal to or less than 15,000 mPa·s at 120° C.

73. The composition of claim 67 wherein said composition has a viscosity equal to or less than 12,000 mPa·s at 120° C.

74. The composition of claim 67 wherein the end-block tackifying resin is a product from pure monomer polymerization.

75. The composition of claim 67 wherein the end-block tackifying resin has a softening point of from 50 to 120° C.

76. The composition of claim 67 wherein the end-block tackifying resin has a softening point of from 70 to 115° C.

77. The composition of claim 67 having about 50% to about 62% by weight of said first midblock tackifying resin.

78. The composition of claim 67 wherein said composition has an initial bond retention of at least about 70%.

79. The composition of claim 67 wherein said composition has an initial bond retention of at least about 75%.

80. The composition of claim 67 wherein said composition has an initial bond retention of at least about 80%.

81. The composition of claim 67 further having a one-week-aged bond retention of at least about 50%.

82. The composition of claim 67 further having a one-week-aged bond retention of at least about 60%.

83. The composition of claim 67 further having a one-week-aged bond retention of at least about 70%.

84. The composition of claim 67 wherein the mid-block tackifying resin has an aromaticity content of at least 1.5% by weight and is selected from the group consisting of aliphatic hydrocarbon resins and their hydrogenated derivatives, hydrogenated cycloaliphatic hydrocarbon resins, aromatic modified aliphatic or hydrogenated cycloaliphatic hydrocarbon resins, aliphatic modified aromatic hydrocarbon resins, partially or fully hydrogenated aromatic hydrocarbon resins, polyterpene and styrenated polyterpene resins.

85. The composition of claim 67 further including a plasticizer is selected from the group consisting of mineral oil and liquid polybutene.

86. The composition of claim 67 wherein further including a wax is selected from the group consisting of petroleum waxes, microcrystalline waxes, low molecular weight polyethylene and polypropylene, synthetic waxes and polyolefin waxes.

87. The composition of claim 67 wherein said elastic modulus G' is higher than about 6000 Pa.

88. The composition of claim 67 wherein said viscous modulus G" is between about 50 Pa and about 500 Pa.

89. The composition of claim 67 wherein said tan delta value is between about 1 and about 50.

90. The composition of claim 67 wherein said tan delta value is between about 2 and about 30.

91. A hot melt adhesive composition, comprising a blend of the following components:
   about 10% to about 25% by weight of an elastomeric block copolymer having a structure represented by A-B, A-B-A, A-(B-A)$_n$-B, or (A-B)$_n$-Y wherein A comprises a polyvinyl aromatic block having a Tg higher than 80° C., B comprises a rubbery midblock having a Tg lower than −10° C., Y comprises a multivalent compound, and n is an integer of at least 3, and wherein said block copolymer is a mixture of an SIS block copolymer having a styrene content of about 14% to about 35% by weight, and a block copolymer which is selected from the group consisting of SB, SIBS, SEBS, SEP, SEPS, SBBS, SEEPS and blends thereof;
   about 40% to about 65% by weight of a first midblock tackifying resin having a softening point of about 110° C. to about 125° C. and having an aromatic content of at least about 1.5% by weight;
   about 0 to 55% of second midblock tackifying resin;
   about 14% to about 35% by weight of a liquid plasticizer; and
   about 0% to about 20% by weight of an end block tackifying resin having a softening point lower than 125° C.;
   wherein the components total 100% by weight of the composition, the viscosity of the composition is equal to or less than about 20,000 mPa·s at 120° C., and may be applied by spraying at a temperature lower than 150° C. and initial bond retention of the composition on elastic strands is at least about 60%.

92. A hot melt adhesive composition, comprising a blend of the following components:
   about 10% to about 25% by weight of an elastomeric block copolymer having a structure represented by A-B, A-B-A, A-(B-A)$_n$-B, or (A-B)$_n$-Y wherein A comprises a polyvinyl aromatic block having a Tg higher than 80° C., B comprises a rubbery midblock having a Tg lower than −10° C., Y comprises a multivalent compound, and n is an integer of at least 3, and wherein said block copolymer is a mixture of an SBS block copolymer having a styrene content of about 20% to about 45% by weight, and a block copolymer which is selected from the group consisting of SB, SIBS, SEBS, SEP, SEPS, SBBS, SEEPS and blends thereof;
   about 40% to about 65% by weight of a first midblock tackifying resin having a softening point of about 110° C. to about 125° C. and having an aromatic content of at least about 1.5% by weight;
   about 0 to 55% of second midblock tackifying resin;
   about 14% to about 35% by weight of a liquid plasticizer; and
   about 0% to about 20% by weight of an end block tackifying resin having a softening point lower than 125° C.;
   wherein the components total 100% by weight of the composition, the viscosity of the composition is equal to or less than about 20,000 mPa·s at 120° C., and may be applied by spraying at a temperature lower than 150° C. and initial bond retention of the composition on elastic strands is at least about 60%.

* * * * *